(12) United States Patent
Seymore et al.

(10) Patent No.: US 11,862,037 B1
(45) Date of Patent: Jan. 2, 2024

(54) METHODS AND DEVICES FOR DETECTION OF EATING BEHAVIOR

(71) Applicant: Amazon Technologies, Inc., Seattle, WA (US)

(72) Inventors: David Lawrence Seymore, Seattle, WA (US); Leo Benedict Baldwin, Seattle, WA (US); David Heckerman, Bellevue, WA (US); Michael Vogelsong, Seattle, WA (US); Maulik Majmudar, Medina, WA (US)

(73) Assignee: Amazon Technologies, Inc., Seattle, WA (US)

( * ) Notice: Subject to any disclaimer, the term of this patent is extended or adjusted under 35 U.S.C. 154(b) by 1111 days.

(21) Appl. No.: 16/453,449

(22) Filed: Jun. 26, 2019

(51) Int. Cl.
| *G09B 19/00* | (2006.01) |
| *G16H 20/60* | (2018.01) |
| *A61B 5/00* | (2006.01) |
| *A61B 5/145* | (2006.01) |
| *A61B 5/0205* | (2006.01) |
| *A61B 5/318* | (2021.01) |
| *A61B 5/024* | (2006.01) |

(52) U.S. Cl.
CPC ........ *G09B 19/0092* (2013.01); *A61B 5/0205* (2013.01); *A61B 5/14517* (2013.01); *A61B 5/14532* (2013.01); *A61B 5/318* (2021.01); *A61B 5/681* (2013.01); *A61B 5/742* (2013.01);

*G16H 20/60* (2018.01); *A61B 5/02438* (2013.01); *A61B 2562/0204* (2013.01)

(58) Field of Classification Search
CPC ........................... G09B 19/0092; G16H 20/60
See application file for complete search history.

(56) References Cited

U.S. PATENT DOCUMENTS

| 11,138,901 B1 * | 10/2021 | Angel ...................... G06T 7/62 |
| 2010/0332571 A1 * | 12/2010 | Healey ................... G06Q 50/12 |
| | | 715/810 |
| 2014/0347491 A1 * | 11/2014 | Connor ................. A61B 5/1114 |
| | | 348/158 |
| 2016/0350514 A1 * | 12/2016 | Rajendran .............. G06Q 10/10 |
| 2017/0220772 A1 * | 8/2017 | Vleugels ................ G16H 50/70 |
| 2018/0242908 A1 * | 8/2018 | Sazonov .............. A61B 5/4542 |
| 2018/0293249 A1 * | 10/2018 | Tabares ................. H04W 4/023 |
| 2019/0038186 A1 * | 2/2019 | Tanriover ............. A61B 5/4542 |

* cited by examiner

*Primary Examiner* — Jay Trent Liddle
*Assistant Examiner* — Alyssa N Brandley
(74) *Attorney, Agent, or Firm* — Eversheds Sutherland (US) LLP

(57) ABSTRACT

Systems, devices, and methods are provided for detecting and correcting eating behavior. A device may receive audio data, determine that the audio data is indicative of consumption of a product by a user. The device may determine, based on the product, a measureable attribute associated with the user. The device may receive first data associated with the measureable attribute. The device may determine that the first data exceeds a threshold. The device may generate a message for presentation.

18 Claims, 9 Drawing Sheets

METHODS AND DEVICES FOR DETECTION OF EATING BEHAVIOR

BACKGROUND

To address health issues related to the consumption of food, beverage, or other products, medical professionals may recommend consuming more or less of certain types of products. In addition, devices may monitor biomedical characteristics of patients, allowing patients and medical professionals to address health-related issues. Some methods of monitoring the effects of consumable products on patients may be inconvenient and ineffective.

Figure 1:
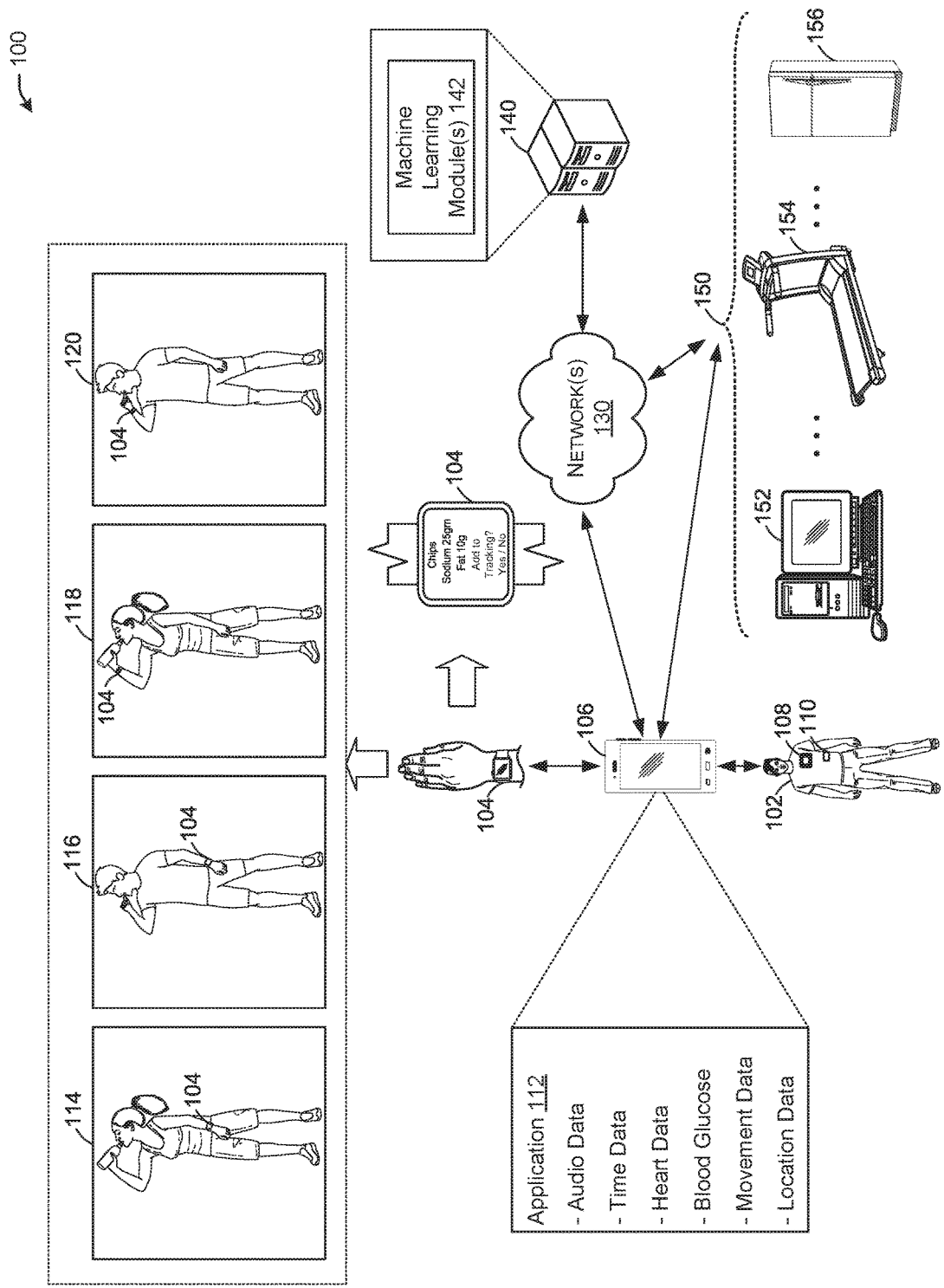
FIG. 1 illustrates an example system for detection and correction of eating behavior, in accordance with one or more example embodiments of the present disclosure.

Certain implementations will now be described more fully below with reference to the accompanying drawings, in which various implementations and/or aspects are shown. However, various aspects may be implemented in many different forms and should not be construed as limited to the implementations set forth herein; rather, these implementations are provided so that this disclosure will be thorough and complete, and will fully convey the scope of the disclosure to those skilled in the art. Like numbers refer to like elements throughout. Hence, if a feature is used across several drawings, the number used to identify the feature in the drawing where the feature first appeared will be used in later drawings.

DETAILED DESCRIPTION

Overview

Example embodiments described herein provide certain systems, methods, and devices for detection and correction of eating behavior.

Consumable products, such as foods, beverages, nutritional products, vitamins, pharmaceuticals, biologics, and others, may cause effects on people who consume them. For example, because some carbohydrates may be broken down into sugar, such as glucose, some foods high in carbohydrates may cause an increase in a person's blood sugar. Alcohol content may cause an increase in a person's blood alcohol levels or heart rate. Foods or beverages with high fat, salt, or caloric content may cause higher blood pressure. Caffeine may increase a person's heart rate.

Consumable products also may exhibit characteristics associated with their consumption. For example, the opening of a can or bottle with a carbonated beverage may exhibit a distinct sound. The chewing of crunchy food such as potato chips may sound different than the chewing of an apple.

Patients and medical professionals may benefit from customizing the monitoring of biomedical data based on when and what a patient may be consuming. For example, the sampling rate for a person's heartrate may increase when a person eats or drinks to better capture the effects of the consumable product on the person, and the movement or activity of a person may be monitored differently when a user is consuming a product. Because an audio sampling may be captured at a low frequency at small intervals, the audio sampling may result in the capture of audio data used to identify when a person is eating or drinking, and to trigger a higher frequency sampling or higher sampling rate for more detailed data collection.

Therefore, by detecting audio associated with consumption of a product and/or opening of a package, the process for determining that someone is consuming a consumable product and identifying that consumable product may be automated. By identifying biomedical data which may be affected by the consumption of a particular type of consumable product, additional data including the biomedical data may be monitored in customizable ways for the effects that the consumable product has on the person who consumed the product. In this manner, systems, devices, and methods may detect eating and drinking behavior, and may correct the behavior by encouraging a person to avoid consuming certain products or to substitute healthier alternative products.

In one or more embodiments, a wearable device such as a watch, a ring, glasses, headbands, or medical device may record audio (with a user's consent) using one or more audio sensors (e.g., microphones, electromyography sensors). Captured audio data may be analyzed by the device or sent to another device for analysis. The audio data may be converted to a sound profile. For example, a sound profile may include a frequency distribution of captured audio signals over time. A device may compare the sound profile to known sound profiles of consumable products. For example, the crunch of potato chips may match a known sound profile for potato chips. The crisp sound of a user biting into an apple may have a distinct sound profile, as may the sound of swallowing a liquid, opening a carbonated beverage or bag, opening and closing a refrigerator, an active microwave, and the like. Audio profiles of consumable products may be differentiated from audio profiles of other types of noises or sounds, such as talking (e.g., voice) or certain types of background noise (e.g., sounds of musical instruments, automobiles, computer devices, etc.). Machine learning using neural networks or other types of machines may be used to identify sounds and words to identify when a user is consuming a product, about to consume a product, and has recently consumed a product. Using sound profiles, a device may determine a specific product or type of product that a person may be consuming.

In one or more embodiments, a device may determine characteristics of a product once the product has been identified. For example, a cheeseburger may have high cholesterol and may trigger a higher blood pressure for a person, as may potato chips or other foods known to be salty. Candy may include sugar which may cause an increase in a person's blood glucose levels. Spicy or acidic products may cause indigestion or acid reflux. A caffeinated product may increase a person's heart rate. When a device determines the product or type of product that a person may be consuming, the device may determine corresponding characteristics of the product, and may determine data which may be associated with the effects of the characteristics. For example, if a characteristic of a sugary food or drink is to increase blood glucose levels, a device may determine that blood glucose data may indicate the effects of consuming the sugary food or drink. If caffeine products are known to increase heartrate, a device may determine that monitoring a user's heartrate may provide an indication of the effects of consuming caffeine.

In one or more embodiments, a device may determine that another device or an application is responsible for detecting or otherwise collecting data associated with a characteristic of a consumable product. For example, a blood glucose monitor may measure blood glucose levels. A heartrate monitor may capture heartrate data. A hydration sensor may measure a user's dehydration. A pacemaker may recognize a person's electrocardiogram. A thermometer may measure a person's temperature. An accelerometer, magnetometer, wireless signals (e.g., Bluetooth or Wi-Fi signals), global navigation satellite system signals may be used (with a user's consent) to determine a device's motion or location, and the motion or location data may confirm if the user is at a location (e.g., a restaurant) or moving (e.g., motioning an arm or hand toward the face) in a manner which indicates a likely consumption of a product (e.g., and may be used to supplement audio data for the purpose of determining when a user is consuming a product). A hydrogen sensor may measure a user's indigestion. When a device determines a characteristic of a consumable product and an associated type of data which may measure the effects of the characteristic on a person consuming the consumable product, the device may identify another device or an application responsible for capturing the associated type of data, and may request the associated data. The request for the data may include specification of a sampling rate or frequency. For example, one device may request that another device provide data captured at a particular rate or frequency (e.g., a higher sampling rate or frequency than normal). Such may allow devices to conserve power and resources (e.g., by not sampling at higher rates or frequencies unless a user is consuming something).

In one or more embodiments, with a user's consent, a device may help a user regulate their intake of consumable products and may provide recommendations for products, when to consume or not consume, locations where consumable products are available, nutritional information, warnings/alerts, alarms to medical professionals or other parties or devices, and the like. For example, when a device detects that a user is eating food late at night (e.g., outside of a normal window of time associated with eating meals), the device may present alarms or messages encouraging the user to eat something healthier or to wait until the next meal, or to indicate the effects that consuming a product may have on the person. The device may provide recommendations of healthier products to substitute, such as substituting fruit and vegetables for a less healthy product.

In one or more embodiments, devices may connect to one another using a variety of connection methods such as Wi-Fi, Bluetooth, and ultrasound, and may use direct or other peer-to-peer connections (e.g., Wi-Fi Direct, neighbor awareness networking, etc.) to communicate with one another. For example, a smart phone, tablet, or other mobile device may execute applications which may collect data from other devices, such as heartrate monitors, blood glucose monitors, pacemakers, thermometers, hydrogen sensors, exercise monitors, step monitors, and the like. A device may capture audio, and when the audio indicates a user's consumption of a product, the device may request that a biomedical sensor or another mobile device in communication with the biomedical sensor provide other data, such as additional audio data, biomedical data, user profile or preference data, and the like. A device may collect such data, with user consent, and may analyze the data to determine that a user is consuming a product, what the product is, characteristics of the product, data indicative of or effected by the characteristics, and the effects of the product on a person. When audio data is strongly indicative of consumption (e.g., a confidence level associated with the sound profile of a consumable product exceeds a threshold confidence), the data collected by a mobile device may be analyzed for the effects that a consumable product has on a person. When the confidence level associated with the sound profile of a consumable product does not exceed a threshold confidence, data may be collected from or sent to a remote service (e.g., a cloud server) for analysis or collection.

In one or more embodiments, time and duration of consumption may be indicative of an amount of a product consumed and/or when the product is consumed. If audio data indicates that a user is consuming products outside of normal meal times or that a user is consuming products for a long time (e.g., longer than a time threshold), a device may determine that a user may be consuming too much, too little, and/or consuming products and unhealthy times of day (e.g., right before sleeping). Such may trigger the generation of messages or alarms, and/or the capturing of relevant biomedical data to monitor.

The above descriptions are for purposes of illustration and are not meant to be limiting. Numerous other examples, configurations, processes, etc., may exist, some of which are described in greater detail below. Example embodiments will now be described with reference to the accompanying figures.

Illustrative Processes and Use Cases

FIG. 1 illustrates an example system 100 for detection and correction of eating behavior, in accordance with one or more example embodiments of the present disclosure.

Referring to FIG. 1, the system 100 may include a user 102 wearing a wearable device 104 shown as a watch. The user 102 may have a user device 106, which may be in communication with one or more biomedical devices (e.g., device 108, device 110). The user device 106 may collect data using one or more applications (e.g., application 112). For example, the application 112 may collect audio data captured by the wearable device 104, time data (e.g., a time of day, a duration associated with captured data), heart data (e.g., heartrate data or electrocardiogram data captured by the device 108), blood glucose data (e.g., captured by the device 108 or the device 110), movement data (e.g., captured by the user device 106), and location data (e.g., as captured by the user device 106). The data captured by the wearable device 104, the user device 106, the device 108, and/or the device 110 may be collected with user consent (e.g., the user may be prompted to confirm whether to allow data to be collected and/or tracked).

Still referring to FIG. 1, the wearable device 104 may capture (e.g., record) audio data of the user 102 (with user consent) consuming one or more consumable products according to a variety of scenarios. In scenario 114, a user may be drinking a liquid with one hand, and wearing the wearable device 104 with the other hand/arm. In scenario 116, a user may be eating a product with one hand, and wearing the wearable device 104 with the other hand/arm. In scenario 118, a user may be drinking a liquid with the same hand/arm wearing the wearable device 104. In scenario 120, a user may be eating a product with the same hand/arm wearing the wearable device 104. In any scenario, the wearable device 104 may capture audio such as chewing, swallowing, opening a package or container (e.g., a bottle, can, bag, box, jar, etc.), opening or closing a refrigerator or microwave, or audio of a person talking (e.g., audio including keywords regarding the consumption of a product or location where consumable products may be sold).

Still referring to FIG. 1, the user device 106 may communicate (e.g., using one or more communication networks 130) with one or more servers 140 (e.g., cloud-based servers), and with one or more devices 150 (e.g., computer device 152, treadmill 154, refrigerator 156) using the one or more communication networks 130 or using a direct connection (e.g., Wi-Fi, Bluetooth, ultrasound). The one or more servers 140 may receive data captured by the wearable device 104, the user device 106, the device 108, the device 110, and/or the one or more devices 150 and may analyze the data, or any combination of the one or more servers 140, the user device 106, and the wearable device 104 may analyze the captured data. With user consent, the one or more servers 140 may provide user data, such as health data, data regarding the user's product consumption habits and history, exercise and other activity data, and the like. The one or more devices 150 may provide data indicating when a user exercised or bought consumable products (e.g., using browsing or other search history from the computer device 152, or medical data such as medical history or prescription product history from the computer device 152). Such data from the one or more devices 150 may indicate activity options (e.g., exercising options available to a user) and for analysis regarding whether a user is exercising after consuming certain types of products.

In one or more embodiments, the user device 106 may include any suitable processor-driven device including, but not limited to, a mobile device or a non-mobile (e.g., a static) device. For example, the user device 106 may include, a user equipment (UE), a station (STA), an access point (AP), a software enabled AP (SoftAP), a personal computer (PC), a wearable wireless device (e.g., bracelet, watch, glasses, ring, etc.), a desktop computer, a mobile computer, a laptop computer, an Ultrabook™ computer, a notebook computer, a tablet computer, a server computer, a handheld computer, a handheld device, an internet of things (IoT) device, a sensor device, a PDA device, a handheld PDA device, an on-board device, an off-board device, a hybrid device (e.g., combining cellular phone functionalities with PDA device functionalities), a consumer device, a vehicular device, a non-vehicular device, a mobile or portable device, a non-mobile or non-portable device, a mobile phone, a cellular telephone, a PCS device, a PDA device which incorporates a wireless communication device, a mobile or portable GPS device, a DVB device, a relatively small computing device, a non-desktop computer, a "carry small live large" (CSLL) device, an ultra mobile device (UMD), an ultra mobile PC (UMPC), a mobile internet device (MID), an "origami" device or computing device, a device that supports dynamically composable computing (DCC), a context-aware device, a video device, an audio device, an A/V device, a set-top-box (STB), a blu-ray disc (BD) player, a BD recorder, a digital video disc (DVD) player, a high definition (HD) DVD player, a DVD recorder, a HD DVD recorder, a personal video recorder (PVR), a broadcast HD receiver, a video source, an audio source, a video sink, an audio sink, a stereo tuner, a broadcast radio receiver, a flat panel display, a personal media player (PMP), a digital video camera (DVC), a digital audio player, a speaker, an audio receiver, an audio amplifier, a gaming device, a data source, a data sink, a digital still camera (DSC), a media player, a smartphone, a television, a music player, or the like. Other devices, including smart devices such as lamps, climate control, car components, household components, appliances, etc. may also be included in this list.

In one or more embodiments, the user device 106 may execute one or more applications, such as the application 112, which may collect biomedical and/or other data from the device 108 and/or the device 110. For example, the device 108 and/or the device 110 may include a blood glucose monitor, a heartrate monitor, electrodes, a pacemaker, a thermometer, a hydration monitor, a hydrogen sensor, or other sensors or devices capable of detecting user data with a user's consent. One or more applications executable by the user device 106 may collect and analyze data from the device 108 and/or the device 110, and may send the data to the one or more servers 140 for analysis, or may analyze the data locally on the user device 106. The analysis of the data may be supplemented by data from the one or more devices 150 (e.g., to determine user purchasing and/or exercising habits).

In one or more embodiments, the wearable device 104 may include a wearable wireless device (e.g., bracelet, watch, glasses, ring, etc.) capable of capturing audio with one or more sensors (e.g., one or more microphones and/or electromyography sensors, not shown). The one or more sensors may be arranged to detect sounds at different levels and/or in different ranges or directions from the wearable device 104. The use of multiple sensors may allow for noise cancelation (e.g., background noise suppression) while preserving sounds relevant to consumption of a product. The audio data may be analyzed by the wearable device 104, the user device 106, and/or the one or more servers 140 to determine whether the audio data indicates that the user 102 is consuming a product. For example, captured audio data may be analyzed by the wearable device 104 or sent to another device (e.g., the user device 106 or the one or more servers 140) for analysis. The audio data may be converted to a sound profile. For example, a sound profile may include a frequency distribution of captured audio signals over time. The wearable device 104, the user device 106, or the one or more servers 140 may compare the sound profile to known sound profiles of consumable products. For example, the crunch of potato chips may match a known sound profile for potato chips. The crisp sound of a user biting into an apple may have a distinct sound profile, as may the sound of swallowing a liquid, opening a carbonated beverage or bag, opening and closing a refrigerator, an active microwave, and the like. Audio profiles of consumable products may be differentiated from audio profiles of other types of noises or sounds, such as talking (e.g., voice) or certain types of background noise (e.g., sounds of musical instruments, automobiles, computer devices, etc.). Machine learning modules 142 may use neural networks or other types of machines (e.g., implemented by the one or more servers 140) may be used to identify sounds and words to identify when a user is consuming a product, about to consume a product, and has recently consumed a product. Using sound profiles, the wearable device 104, the user device 106, or the one or more servers 140 may determine a specific product or type of product that a person may be consuming.

In one or more embodiments, when captured audio by the wearable device 104 or another device matches an audio profile of a consumable product, the wearable device 104, the user device 106, or the one or more servers 140 may determine one or more characteristics associated with the consumable product. For example, a cheeseburger may have high cholesterol and may trigger a higher blood pressure for a person, as may potato chips or other foods known to be salty. Candy may include sugar which may cause an increase in a person's blood glucose levels. Spicy or acidic products may cause indigestion or acid reflux. A caffeinated product may increase a person's heart rate. When the wearable device 104, the user device 106, or the one or more servers 140 determines the product or type of product that a person may be consuming, the wearable device 104, the user device 106, or the one or more servers 140 may determine corresponding characteristics of the product, and may determine data which may be associated with the effects of the characteristics. For example, if a characteristic of a sugary food or drink is to increase blood glucose levels, the wearable device 104, the user device 106, or the one or more servers 140 may determine that blood glucose data may indicate the effects of consuming the sugary food or drink. If caffeine products are known to increase heartrate, the wearable device 104, the user device 106, or the one or more servers 140 may determine that monitoring a user's heartrate may provide an indication of the effects of consuming caffeine.

In one or more embodiments, when the wearable device 104, the user device 106, or the one or more servers 140 determines one or more characteristics associated with a consumable product, the wearable device 104, the user device 106, or the one or more servers 140 may determine a measurable attribute to capture, an application (e.g., the application 112) that may capture data indicative of the measurable attribute, and/or a device (e.g., the device 108, the device 110, the one or more devices 150) associated with capturing and/or providing the data indicative of the measurable characteristic. The measurable attribute may include blood glucose levels or other blood sugar levels, heartrate, electrocardiogram data, hydrogen data, breathing data, perspiration data, movement or activity data, biomedical cell data, skin data, tissue data, circulatory data, blood content, blood alcohol data, and the like. With user consent, the wearable device 104, the user device 106, or the one or more servers 140 may determine which device and/or application may provide such data for the measurable attribute.

In one or more embodiments, when the wearable device 104, the user device 106, or the one or more servers 140 determines a device and/or application which may capture and provide data for the measurable attribute associated with a characteristic of a consumable product, the wearable device 104, the user device 106, or the one or more servers 140 may request the data for the measurable attribute at a particular sampling rate or frequency. For example, a device may sample the data for the measurable characteristic at one sampling rate or frequency, and the wearable device 104, the user device 106, or the one or more servers 140 may request that the sampling rate or frequency be increased at least for a time period (e.g., until it is determined that the user is no longer consuming the product or a threshold time after consumption of the product). The wearable device 104, the user device 106, or the one or more servers 140 may receive the data captured at an increased frequency or sampling rate, allowing the capturing device to conserve resources by sampling at a lower frequency or sampling rate outside of requests from the wearable device 104, the user device 106, or the one or more servers 140.

In one or more embodiments, the wearable device 104, the user device 106, or the one or more servers 140 may receive captured data associated with a measurable attribute, may analyze the data, and may determine an association between the data of the measurable attribute and the product, along with similar products. The wearable device 104, the user device 106, or the one or more servers 140 may store data associated with a user and with a product that indicates user reactions associated with the measurable attribute (e.g., changes in heartrate, blood sugar, hydration levels, breathing levels, heart waves, blood pressure, neurological data, and the like).

In one or more embodiments, the wearable device 104, the user device 106, or the one or more servers 140 may generate one or more messages, alarms, or alerts based on the data. For example, if the wearable device 104, the user device 106, or the one or more servers 140 determines from prior association data that a product or similar product causes a negative biomedical effect of a user, the wearable device 104, the user device 106, or the one or more servers 140 may generate a message or alarm intended to discourage the user from consuming the product, may recommend substitute products known to cause less of the biomedical effect (e.g., not associated with the consumable product's characteristics), and/or may send alerts to other devices to let other users know that the person is consuming a product known to cause a negative biomedical effect. As shown in FIG. 1, the wearable device 104 may display nutritional information, including the content of sodium and fat, along with a recommendation to try a healthier product (e.g., to substitute an apple for salty potato chips). Messages and alerts may provide any combination of information related to a user's health (e.g., heartrate, blood glucose, blood pressure, etc.), information about what the user is consuming (e.g., nutritional information, health-related effects, etc.), messages to encourage or discourage consumption of certain products, offers for similar or substitute products, notifications of locations where products may be purchased, notifications regarding a user's exercise habits and/or exercise options and locations (e.g., that the treadmill 154 or other exercise equipment like an exercise bicycle are available and have not been used since a given time), and the like.

In one or more embodiments, with user consent, recording audio or other data by the wearable device 104 may activate or change based on a time, location, position, or movement of the wearable device 104. For example, when a time of day is within a selected or known meal time (e.g., a range of time in the morning for breakfast, a range of time in the afternoon for lunch, a range of time in the evening for dinner), the wearable device 104 may activate recording or increase sampling frequency. In this manner, activation may include initiating or powering on one or more components of the wearable device 104 (e.g., such as microphones or other audio sensors), and may include adjusting a sampling rate or frequency. When the wearable device 104 is in a position or orientation associated with consumption of a product, the wearable device 104 may activate recording or increase sampling frequency. For example, using accelerometer, magnetometer, or other device data, the wearable device 104 may determine that a user's arm or hand is at an angle (e.g., within an angular range) with respect to one or more additional sensors on other devices and/or with respect to gravity known to be associated with bringing a consumable product to a user's face for consumption.

In one or more embodiments, with user consent, when the wearable device 104 is in such a position or orientation, the wearable device 104 may activate a timer to determine the duration that the wearable device 104 is in the position or orientation. The timer may capture time indicating a duration (e.g., how long a user is consuming a product), which may be correlated with an amount of product consumption (e.g., the longer the duration, the more product is consumed). The wearable device 104 may deactivate recording or decrease sampling frequency when the wearable device 104 determines that it is no longer in a consumption position or orientation. The wearable device 104 may determine the time at which a user may be consuming a product, and may generate messages based on the time (e.g., to not eat in between meals). The wearable device 104 may use global navigation satellite system data, Wi-Fi data, Bluetooth data, ultrasound data, accelerometer data, magnetometer data, or other data to identify its location. The wearable device 104 may determine (e.g., using a map or other type of application executable on the wearable device 104 or by the user device 106) whether the device's current location is at or near (e.g., within a distance threshold) of a restaurant or other provider of consumable products, and may generate offers, incentives, alternative options, or messages discouraging the consumption of certain products.

In one or more embodiments, to identify products based on what the user is determined to be consuming, the wearable device 104, the user device 106, and/or the one or more servers 140 may use product identifiers. For example, when audio data matches a sound profile associated with consumption of a product, the product may have a product identifier. The wearable device 104, the user device 106, and/or the one or more servers 140 may store and/or access data including related or different products. For example, given a product identifier, the wearable device 104, the user device 106, and/or the one or more servers 140 may identify other products having similar characteristics (e.g., health characteristics, nutritional content, types of products, a same brand, same effects on a person's health, such as decreased heartrate or blood pressure, etc.) or substitute products (e.g., healthier products not known to cause the same level of effects such as heartrate or blood pressure changes, products with less content of certain ingredients such as sugar or fat, etc.).

In one or more embodiments, the one or more communications networks 130 may include, but not limited to, any one of a combination of different types of suitable communications networks such as, for example, broadcasting networks, cable networks, public networks (e.g., the Internet), private networks, wireless networks, cellular networks, or any other suitable private and/or public networks. Further, any of the one or more communications networks 130 may have any suitable communication range associated therewith and may include, for example, global networks (e.g., the Internet), metropolitan area networks (MANs), wide area networks (WANs), local area networks (LANs), or personal area networks (PANs). In addition, any of the one or more communications networks may include any type of medium over which network traffic may be carried including, but not limited to, coaxial cable, twisted-pair wire, optical fiber, a hybrid fiber coaxial (HFC) medium, microwave terrestrial transceivers, radio frequency communication mediums, white space communication mediums, ultra-high frequency communication mediums, satellite communication mediums, or any combination thereof.

Figure 2:
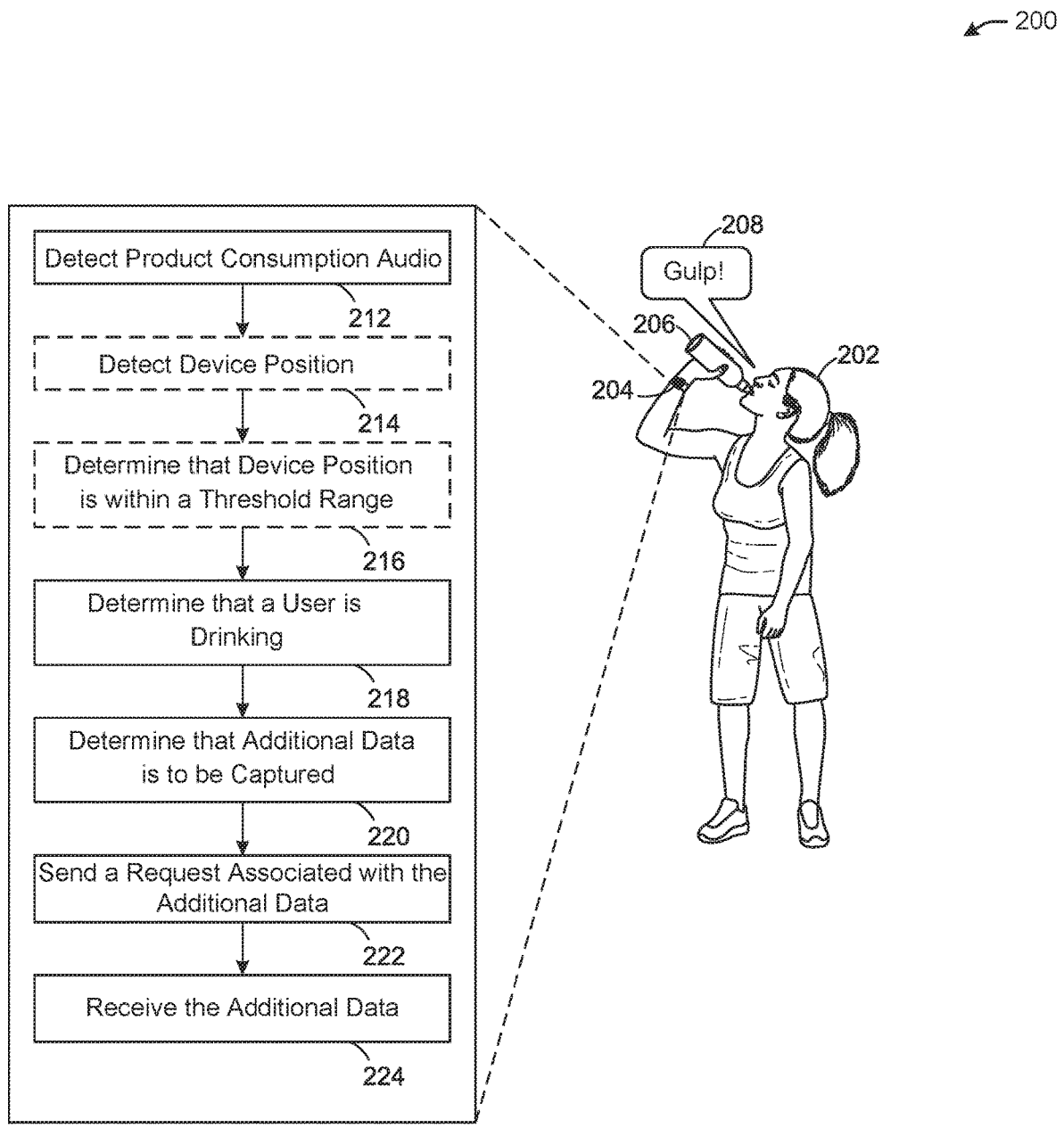
FIG. 2 illustrates an example process for detection and correction of eating behavior, in accordance with one or more example embodiments of the present disclosure.

FIG. 2 illustrates an example process 200 for detection and correction of eating behavior, in accordance with one or more example embodiments of the present disclosure.

Referring to FIG. 2, a person 202 wearing a wearable device 204 (e.g., having functionality as described with regard to the wearable device 104 of FIG. 1) may consume a product 206 (e.g., a liquid or type of beverage). With user consent, the wearable device 204 may capture audio 208 of the person 202 consuming the product (e.g., a swallowing sound). At block 212 of the process 200, the wearable device 204 may detect the audio 208 (e.g., using one or more microphones or other audio sensors). The audio 208 may include chewing, swallowing, opening the product 206, words spoken by the person 202, sounds made by the product 206 (e.g., carbonated beverage sounds), or other audio.

Still referring to FIG. 2, the wearable device 204 optionally may consider its position, orientation, and/or movement. For example, at block 214, the wearable device 204 may detect its position, movement, or orientation (e.g., angles, rotation, movement directions, etc.), and at block 216 may determine that the wearable device 204 is in a position within a threshold range (e.g., angular range indicative of a tilt, height within a threshold distance of a user's face, angular range with respect to gravity or one or more other devices, etc.). Based on the audio 208 and optionally the position, movement, or orientation data, the wearable device at block 218 may determine that the person 202 is consuming the product 206. For example, the wearable device 204 may determine that the audio 208 matches one of more sound profiles for various products or types of products (e.g., food, beverage, etc.). The sound profiles may be ranked (e.g., with respective scores indicating the likelihood that the sound profile matches the audio), and the sound profile with the highest score may be selected. The product or product type corresponding to the selected sound profile may be identified by the wearable device 204 as the product 206.

Still referring to FIG. 2, at block 220, the wearable device 204 may determine that additional data associated with a measurable attribute (e.g., heartrate, blood pressure, blood sugar, etc.) is to be captured. For example, when the product 206 is known (e.g., based on a product profile stored and accessed based on the corresponding product identifier) to have high cholesterol content, the wearable device 204 may determine corresponding characteristics of the product (e.g., increased blood pressure), and may determine data (e.g., blood pressure data) which may be associated with the effects of the characteristic. When a characteristic of a sugary food or drink is to increase blood glucose levels, the wearable device 204 may determine that blood glucose data may indicate the effects of consuming the sugary food or drink. If caffeine products are known to increase heartrate, the wearable device 204 may determine that monitoring a heartrate of the person 202 may provide an indication of the effects of consuming caffeine. The wearable device 204 may determine that another device (e.g., the device 108 or the device 110 of FIG. 1) or an application (e.g., the application 112 of FIG. 1) is responsible for detecting or otherwise collecting data associated with a characteristic of the product 206. At block 222, when the wearable device 204 determines a characteristic of the product 206 and an associated type of data (e.g., a measurable attribute) which may measure the effects of the characteristic on the person 202 consuming the product 206, the wearable device 204 may identify another device (e.g., the device 108 or the device 110 of FIG. 1) or an application (e.g., the application 112 of FIG. 1) responsible for capturing the associated type of data (e.g., as additional data), and may request and receive the associated data. The additional data may include additional audio data, existing audio data, biomedical data, data from one or more other devices, and/or other types of data. The request for the data may include specification of a sampling rate or frequency with which to capture or otherwise detect the additional data. At block 224, the wearable device may receive the additional data.

In one or more embodiments, the request for additional data (e.g., biomedical data) sent by the wearable device 204 may be sent to another device (e.g., the user device 106 of FIG. 1), which may execute one or more applications (e.g., the application 112 of FIG. 1), which may collect biomedical and/or other data from other devices (e.g., the device 108 and/or the device 110 of FIG. 1). The other devices may include a blood glucose monitor, a heartrate monitor, electrodes, a hydration monitor, a hydrogen sensor, or other sensors or devices capable of detecting user data with a user's consent.

In one or more embodiments, the wearable device 204 may include a wearable wireless device (e.g., bracelet, watch, glasses, ring, etc.) capable of capturing audio with one or more sensors (e.g., a microphone, not shown). The audio data may be analyzed by the wearable device 204 or another device to determine whether the audio 208 indicates that the person 202 is consuming the product 206 and what the product 206 is.

In one or more embodiments, the wearable device 204 or another device may analyze the additional data, and may determine an association between the additional data of a measurable attribute and the product 206, along with similar products (e.g., identified using the product identifier for the product 206). The wearable device 204 or another device may store data associated with the person 202 and with the product 206 that indicates user reactions associated with the measurable attribute (e.g., changes in heartrate, blood sugar, hydration levels, breathing levels, heart waves, blood pressure, neurological data, and the like).

In one or more embodiments, the wearable device 204 may generate one or more messages, alarms, or alerts based on the audio 208 and/or the additional data. For example, if the wearable device 204 determines from prior association data that the product 206 or a similar product causes a negative biomedical effect of the person 202 or another person, the wearable device 204 may generate a message or alarm intended to discourage the person 202 from consuming the product 206, may recommend substitute products known to cause less of the biomedical effect (e.g., not associated with the consumable product's characteristics), and/or may send alerts to other devices to let other users know that the person 202 is consuming the product 206 known to cause a negative biomedical effect. The wearable device 204 may display nutritional information, including the content of sodium and fat, along with a recommendation to try a healthier product (e.g., to substitute water for a sugary drink). Messages and alerts may provide any combination of information related to the person's health (e.g., heartrate, blood glucose, blood pressure, etc.), information about what the person 202 is consuming (e.g., nutritional information, health-related effects, etc.), messages to encourage or discourage consumption of certain products, offers for similar or substitute products, notifications of locations where products may be purchased, notifications regarding a user's exercise habits and/or exercise options and locations, and the like.

In one or more embodiments, with user consent, recording the audio 208 or other data by the wearable device 204 may activate or change based on a time, location, position, or movement of the wearable device 204. For example, when a time of day is within a selected or known meal time (e.g., a range of time in the morning for breakfast, a range of time in the afternoon for lunch, a range of time in the evening for dinner), the wearable device 204 may activate recording or increase sampling frequency. In this manner, activation may include initiating or powering on one or more components of the wearable device 204 (e.g., such as microphones or other audio sensors), and may include adjusting a sampling rate or frequency. When the wearable device 204 is in a position or orientation associated with consumption of a product, the wearable device 204 may activate recording or increase sampling frequency. For example, using accelerometer, magnetometer, or other device data, the wearable device 204 may determine that a user's arm or hand is at an angle (e.g., within an angular range) with respect to one or more additional sensors on other devices and/or with respect to gravity known to be associated with bringing a consumable product to a user's face for consumption.

In one or more embodiments, with user consent, when the wearable device 204 is in such a position or orientation, the wearable device 204 may activate a timer to determine the duration that the wearable device 204 is in the position or orientation. The timer may capture time indicating a duration (e.g., how long a user is consuming a product), which may be correlated with an amount of product consumption (e.g., the longer the duration, the more product is consumed). The wearable device 204 may deactivate recording or decrease sampling frequency when the wearable device 204 determines that it is no longer in a consumption position or orientation. The wearable device 204 may determine the time at which a user may be consuming a product, and may generate messages based on the time (e.g., to not eat in between meals). The wearable device 204 may use global navigation satellite system data, Wi-Fi data, Bluetooth data, ultrasound data, accelerometer data, magnetometer data, or other data to identify its location. The wearable device 204 may determine (e.g., using a map or other type of application executable on the wearable device 204) whether the device's current location is at or near (e.g., within a distance threshold) of a restaurant or other provider of consumable products, and may generate offers, incentives, alternative options, or messages discouraging the consumption of certain products.

While FIG. 2 shows the user 202 consuming the product 206 with the same hand/arm that is wearing the wearable device 204, as discussed below with regard to FIG. 3, the wearable device 204 may be used in a similar manner to determine that the person 202 is consuming the product 206 even when the wearable device 204 is worn by the opposite arm/hand (or is at or near another part of the person's body).

Figure 3:
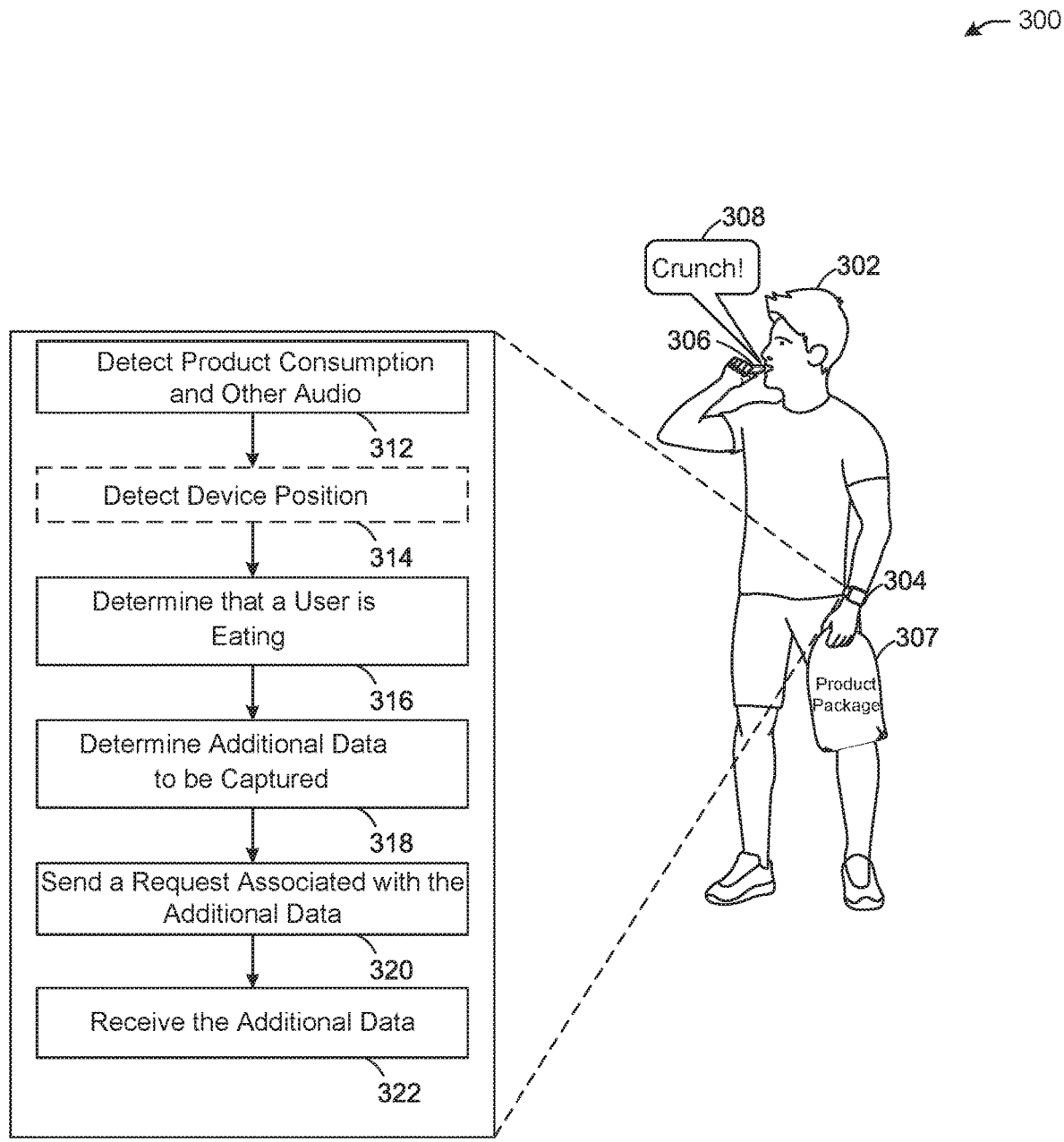
FIG. 3 illustrates an example process for detection and correction of eating behavior, in accordance with one or more example embodiments of the present disclosure.

FIG. 3 illustrates an example process 300 for detection and correction of eating behavior, in accordance with one or more example embodiments of the present disclosure.

Referring to FIG. 3, a person 302 wearing a wearable device 304 (e.g., having functionality as described with regard to the wearable device 104 of FIG. 1) may consume a product 306 (e.g., a food, nutritional product, or other type of consumable product) from a package 307. With user consent, the wearable device 304 may capture audio 308 of the person 302 consuming the product (e.g., a chewing and/or swallowing sound) and/or from the package 307 (e.g., a crinkling sound of a bag, a sound of a top being popped or unscrewed, a sound of a box being ripped open, etc.). At block 312 of the process 300, the wearable device 304 may detect the audio 308 (e.g., using one or more microphones or other audio sensors). The audio 308 may include chewing, swallowing, opening the package 307, words spoken by the person 302, sounds made by the product 306 (e.g., crunchy sounds, chewy sounds, etc.), or other audio.

Still referring to FIG. 3, the wearable device 304 optionally may consider its position, orientation, and/or movement. For example, at block 314, the wearable device 304 may detect its position, movement, or orientation (e.g., angles, rotation, movement directions, etc.), and may determine that the wearable device 304 is in a position within a threshold range. Based on the audio 308 and optionally the position, movement, or orientation data, the wearable device at block 316 may determine that the person 302 is consuming the product 306 (e.g., eating). For example, the wearable device 304 may determine that the audio 308 matches one of more sound profiles for various products or types of products (e.g., food, beverage, etc.). The sound profiles may be ranked (e.g., with respective scores indicating the likelihood that the sound profile matches the audio), and the sound profile with the highest score may be selected. The product or product type corresponding to the selected sound profile may be identified by the wearable device 304 as the product 306.

Still referring to FIG. 3, at block 318, the wearable device 304 may determine that additional data associated with a measurable attribute (e.g., heartrate, blood pressure, etc.) is to be captured. For example, when the product 306 is known (e.g., based on a product profile stored and accessed based on the corresponding product identifier) to be salty (e.g., if the product 306 is a potato chip), the wearable device 304 may determine corresponding characteristics of the product (e.g., increased blood pressure), and may determine data (e.g., blood pressure data) which may be associated with the effects of the characteristic. When a characteristic of a product having high sugar content is to increase blood glucose levels, the wearable device 304 may determine that blood glucose data may indicate the effects of consuming the sugary product. The wearable device 304 may determine that another device (e.g., the device 108 or the device 110 of FIG. 1) or an application (e.g., the application 112 of FIG. 1) is responsible for detecting or otherwise collecting data associated with a characteristic of the product 306. At block 320, when the wearable device 304 determines a characteristic of the product 306 and an associated type of data (e.g., additional data) which may measure the effects of the characteristic on the person 302 consuming the product 306, the wearable device 304 may identify another device (e.g., the device 108 or the device 110 of FIG. 1) or an application (e.g., the application 112 of FIG. 1) responsible for capturing the associated type of data, and may request and receive the associated data. The additional data may include additional audio data, existing audio data, biomedical data, data from one or more other devices, and/or other types of data. The request for the data may include specification of a sampling rate or frequency with which to capture or otherwise detect the additional data. At block 322, the wearable device may receive the additional data.

In one or more embodiments, the request for additional data (e.g., biomedical data) sent by the wearable device 304 may be sent to another device (e.g., the user device 106 of FIG. 1), which may execute one or more applications (e.g., the application 112 of FIG. 1), which may collect biomedical and/or other data from other devices (e.g., the device 108 and/or the device 110 of FIG. 1). The other devices may include a blood glucose monitor, a heartrate monitor, electrodes, a hydration monitor, a hydrogen sensor, or other sensors or devices capable of detecting user data with a user's consent.

In one or more embodiments, the wearable device 304 may include a wearable wireless device (e.g., bracelet, watch, glasses, ring, etc.) capable of capturing audio with one or more sensors (e.g., a microphone, not shown). The audio data may be analyzed by the wearable device 304 or another device to determine whether the audio 308 indicates that the person 302 is consuming the product 306 and what the product 306 is (e.g., the specific product as identified by type and brand, or a type or category of the product 306 such as food, beverage, medicine, nutritional product, fruit, vegetable, snack, candy, burger, chips, water, cola/soda, sugary drink, vitamin, etc.).

In one or more embodiments, the wearable device 304 or another device may analyze the additional data, and may determine an association between the additional data of a measurable attribute and the product 306, along with similar products (e.g., identified using the product identifier for the product 306). The wearable device 304 or another device may store data associated with the person 302 and with the product 306 that indicates user reactions associated with the measurable attribute (e.g., changes in heartrate, blood sugar, hydration levels, breathing levels, heart waves, blood pressure, neurological data, and the like).

In one or more embodiments, the wearable device 304 may generate one or more messages, alarms, or alerts based on the audio 308 and/or the additional data. For example, when the wearable device 304 determines from prior association data that the product 306 or a similar product causes a negative biomedical effect of the person 202 or another person, the wearable device 304 may generate a message or alarm intended to discourage the person 232 from consuming the product 306, may recommend substitute products known to cause less of the biomedical effect (e.g., not associated with the consumable product's characteristics), and/or may send alerts to other devices to let other users know that the person 302 is consuming the product 306 known to cause a negative biomedical effect. The wearable device 304 may display nutritional information, including the content of sodium and fat, along with a recommendation to try a healthier product (e.g., to substitute water for a sugary drink). Messages and alerts may provide any combination of information related to the person's health (e.g., heartrate, blood glucose, blood pressure, etc.), information about what the person 302 is consuming (e.g., nutritional information, health-related effects, etc.), messages to encourage or discourage consumption of certain products, offers for similar or substitute products, notifications of locations where products may be purchased, notifications regarding a user's exercise habits and/or exercise options and locations, and the like.

In one or more embodiments, with user consent, recording the audio 308 or other data by the wearable device 304 may activate or change based on a time, location, position, or movement of the wearable device 304. For example, when a time of day is within a selected or known meal time (e.g., a range of time in the morning for breakfast, a range of time in the afternoon for lunch, a range of time in the evening for dinner), the wearable device 304 may activate recording or increase sampling frequency. In this manner, activation may include initiating or powering on one or more components of the wearable device 304 (e.g., such as microphones or other audio sensors), and may include adjusting a sampling rate or frequency. When the wearable device 304 is in a position or orientation associated with consumption of the product 306, the wearable device 304 may activate recording or increase sampling frequency. For example, using accelerometer, magnetometer, or other device data, the wearable device 304 may determine that a user's arm or hand is at an angle (e.g., within an angular range) with respect to one or more additional sensors on other devices and/or with respect to gravity known to be associated with bringing a consumable product to a user's face for consumption.

In one or more embodiments, with user consent, when the wearable device 304 is in such a position or orientation, the wearable device 304 may activate a timer to determine the duration that the wearable device 304 is in the position or orientation. The timer may capture time indicating a duration (e.g., how long a user is consuming a product), which may be correlated with an amount of product consumption (e.g., the longer the duration, the more product is consumed). The wearable device 304 may deactivate recording or decrease sampling frequency when the wearable device 304 determines that the person 302 is no longer consuming the product (e.g., the audio 308 stops and/or no additional sound is identified from the package 307). The wearable device 304 may determine the time at which a user may be consuming a product, and may generate messages based on the time (e.g., to not eat in between meals). The wearable device 304 may use global navigation satellite system data, Wi-Fi data, Bluetooth data, ultrasound data, accelerometer data, magnetometer data, or other data to identify its location. The wearable device 304 may determine (e.g., using a map or other type of application executable on the wearable device 304) whether the device's current location is at or near (e.g., within a distance threshold) of a restaurant or other provider of consumable products, and may generate offers, incentives, alternative options, or messages discouraging the consumption of certain products.

Figure 4A:
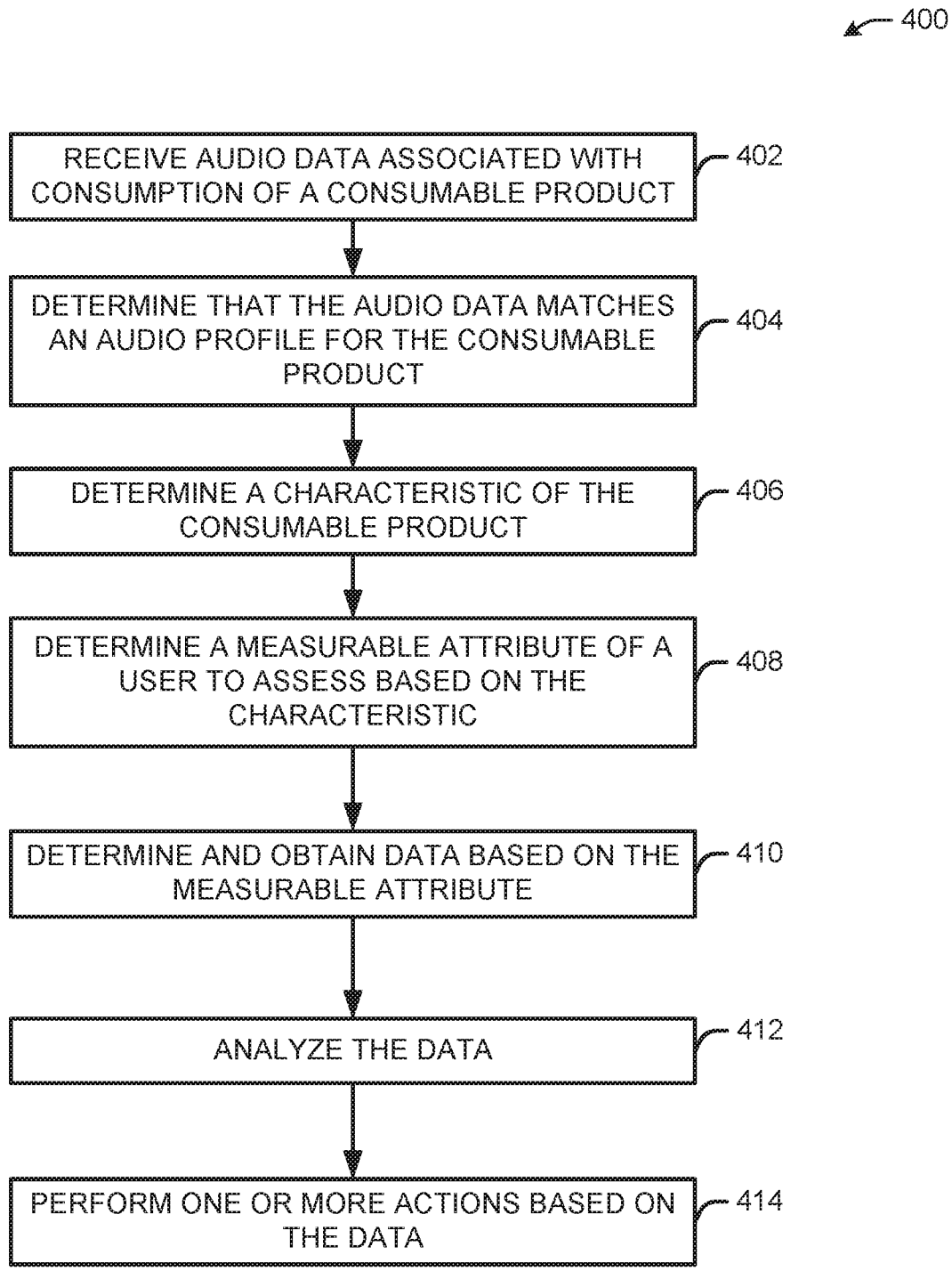
FIG. 4A illustrates a flow diagram for a process for detection and correction of eating behavior, in accordance with one or more example embodiments of the present disclosure.

FIG. 4A illustrates a flow diagram for a process 400 for detection and correction of eating behavior, in accordance with one or more example embodiments of the present disclosure.

At block 402, a device (e.g., the wearable device 104 of FIG. 1), with user consent, may receive audio data associated with the consumption of a consumable product (e.g., the product 206 of FIG. 2, the product 306 and/or the package 307 of FIG. 3). For example, with user consent, the device may record audio with one or more audio sensors (e.g., microphones). The recording may be constant, periodic, based on user input, based on times of day, based on movement, position, or orientation of the device, based on the location of the device (e.g., global positioning coordinates), or the like. In one example, a user may be drinking a liquid with one hand, and wearing the device with the other hand/arm. In another example, a user may be eating a product with one hand, and wearing the device with the other hand/arm. In another example, a user may be drinking a liquid with the same hand/arm wearing the device. In another example, a user may be eating a product with the same hand/arm wearing the device. In any scenario, the device may capture audio such as chewing, swallowing, opening a package or container (e.g., a bottle, can, bag, box, jar, etc.), opening or closing a refrigerator or microwave, or audio of a person talking (e.g., audio including keywords regarding the consumption of a product or location where consumable products may be sold). The device may be worn on a hand, arm, leg, ankle, around the head or neck, or at another location of a body. The product may include any combination of food, beverage, medical products, nutritional products, or any other consumable product.

At block 404, the device may determine that the audio data matches an audio profile for a consumable product or multiple consumable products. For example, the sound of one consumable product may be different when combined with another consumable product. The audio data may be converted to a sound profile. For example, a sound profile may include a frequency distribution of captured audio signals over time. A device may compare the sound profile to known sound profiles of consumable products. For example, the crunch of potato chips may match a known sound profile for potato chips. The crisp sound of a user biting into an apple may have a distinct sound profile, as may the sound of swallowing a liquid, opening a carbonated beverage or bag, opening and closing a refrigerator, an active microwave, and the like. Audio profiles of consumable products may be differentiated from audio profiles of other types of noises or sounds, such as talking (e.g., voice) or certain types of background noise (e.g., sounds of musical instruments, automobiles, computer devices, etc.). Machine learning using neural networks (e.g., the one or more machine learning modules 142 of FIG. 1) or other types of machines may be used to identify sounds and words to identify when a user is consuming a product, about to consume a product, and has recently consumed a product. Using sound profiles, the device may determine a specific product or type of product that a person may be consuming (or combination of products).

At block 406, the device may determine a characteristic of the consumable product or products. For example, when the device determines the product that is being consumed, the device may identify the product and an associated product identifier (or multiple identifiers for a combination of products). The product identifier may be stored on the device or elsewhere (e.g., the user device 106 or the one or more servers 140 of FIG. 1) in addition to characteristics of the product, such as nutrition content, ingredients, product categories, health effects (e.g., changes to blood sugar, blood pressure, cholesterol, heartrate, perspiration, breathing rate, acid reflux, indigestion, fatigue, blood flow, blood alcohol level, medical side effects, etc.).

At block 408, the device may determine, based on the characteristic, one or more measurable attributes of a user to assess. For example, when a characteristic of a product is associated with impacting heartrate, the measurable attribute may be a user's heartrate. When a characteristic is a change in blood pressure, the measurable attribute may be a user's blood pressure. When a characteristic is blood sugar, the measurable attribute may be a user's blood sugar. When the characteristic is blood alcohol, the measurable attribute may be a user's blood alcohol level. When the characteristic is a hydration level, the measurable attribute may be a user's hydration or perspiration. When the characteristic is indigestion or heartburn, the measurable attribute may be a user's hydrogen level. When the characteristic is a known medical side effect, the measurable attribute may be any combination of readings which may indicate whether the side effect is occurring (e.g., breathing, allergic reactions, arrhythmias, etc.). The device may determine another device (e.g., the device 108 or the device 110 of FIG. 1) and/or application (e.g., the application 112 of FIG. 1) which may detect and/or collect data measuring the measurable attribute. For example, when the measurable attribute is a user's heartrate, the device may identify a heartrate monitor and/or an application which may collect heartrate data of a user. When the measurable attribute is blood sugar, the device may identify a glucose monitor and/or application which collects blood glucose data.

At block 410, with user consent, the device may obtain data based on the measurable attribute. In particular, the device may send a request for the data associated with the measurable attribute. For example, when the measurable attribute is heartrate, the request may indicate that heartrate data is requested. When the measurable attribute is blood sugar, the request may indicate that blood sugar data is requested. The request may provide parameters, such as time/duration of the recorded data, and at which sampling rate or frequency. For example, the device which detects or captures the data for the measurable attribute (e.g., a heartrate monitor which captures heartrate data) may capture or detect the data at a sampling rate or frequency. Because of the determination that a user may be consuming a product, the requesting device may request sampling at higher sampling rates or frequencies to collect more data for analysis. The request may indicate multiple sampling rates and frequencies based on different times (e.g., a first sampling rate or frequency at one time, and a second sampling rate or frequency at another time). The measurable attribute may be additional audio data at the same frequency or sampling rate as the previously received audio data, or may be additional audio data at a different frequency or sampling rate. The device may receive the data from the capturing device, or from another device which collects the data (e.g., the user device 106 or the one or more servers 140 of FIG. 1). The device may specify the time for the data to be delivered and in what format. The device may receive the data according to the requested time and/or format. The request may indicate a device or application associated with capturing and/or providing the requested data.

At block 412, with user consent, the device may analyze the data. For example, the device may determine that the data associated with the measurable attribute is further associated with the consumable product. For example, the device may analyze the effects that the consumable product has on a user, and may provide an indication of the effects to be stored with the product identifier for future use. When the effects are a change in heartrate, blood pressure, blood sugar, breathing rate, acid reflux, blood alcohol, perspiration, or the like, the device may associate the effects with the product that was consumed. In this manner, when the device determines a characteristic of a product (e.g., at block 406), the device may consider the effects as characteristics of the product or similar products. The device may determine whether the data confirms the characteristic of the product and/or whether the product was correctly identified. receive the data associated with the measurable attribute. The device may determine that the data exceeds a threshold (e.g., a heartrate threshold, a blood pressure threshold, a blood sugar threshold, an electrocardiography threshold, other biomedical thresholds, a threshold time associated with consumption, etc.). Based on the data exceeding the threshold, the device may determine that consumption of a product has caused the consumer's biomedical data to change, that the user is consuming a product outside of a time range, that the user may be consuming too much or too little of the product, that the user is swallowing or chewing too much or too little, and the like. The messages may be generated to indicate such findings, to recommend adjustments to consumption habits, and the like.

At block 414, with user consent, the device may perform one or more actions based on the data. The device may generate, based on the data, one or more messages for presentation. For example, the messages may display nutrition or other health information related to the product, a representation of the data for the measureable attribute (e.g., an indication that the data shows the user's blood sugar, heartrate, etc. are effected by consumption of the product). The one or more messages may provide product recommendations for similar or different products, may recommend consumption adjustments, may notify other devices that the person is consuming the product at a particular time, may notify the user of exercise options, and more. The device may request additional information for analysis at the same or different frequency or sampling rates. For example, the device may request additional audio data, time data, device data (e.g., orientation data, movement data, location data, etc.). The device may send instructions to other devices (e.g., user devices, smart home devices, exercise equipment, microwaves, refrigerators, etc.), such as instructions to change or stop detection of data, instructions to display messages (e.g., requesting that a person adjust behavior or consumption habits), instructions to log that a user is consuming the product at a given time, etc.

Figure 4B:
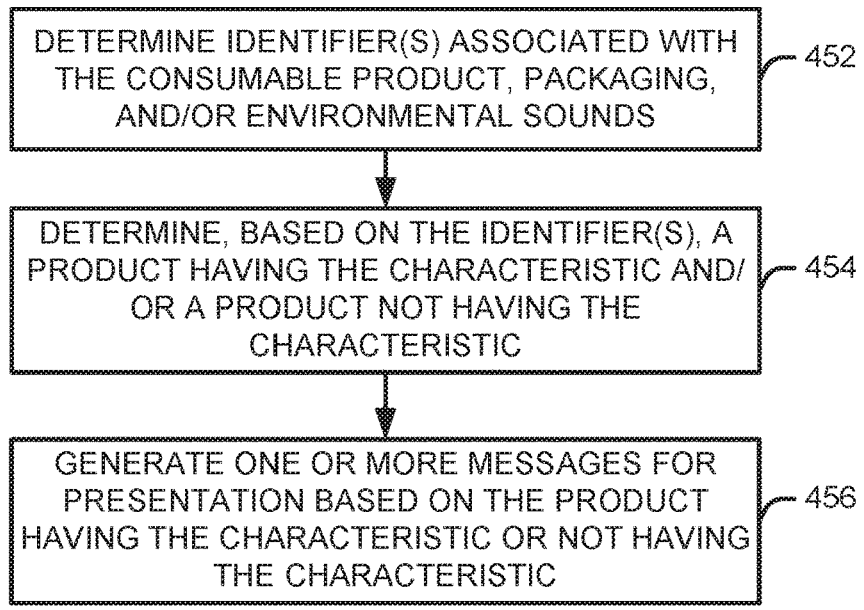
FIG. 4B illustrates a flow diagram for a process for detection and correction of eating behavior, in accordance with one or more example embodiments of the present disclosure.

FIG. 4B illustrates a flow diagram for a process 450 for detection and correction of eating behavior, in accordance with one or more example embodiments of the present disclosure.

At block 452, a device (e.g., the wearable device 104 of FIG. 1) may determine identifiers associated with a consumable product (e.g., the product 206 of FIG. 2, the product 306 of FIG. 3), packaging (e.g., the package 307 of FIG. 3), and/or environmental sounds (e.g., background noises, sounds of devices such as refrigerators, microwaves, cooking appliances, product storage, etc.). For example, when audio data matches a sound profile associated with consumption of a product, the product may have a product identifier. Packaging, such as bottles, cans, bags, boxes, containers, etc. may have product identifiers. Environmental sounds may have identifiers. Any combination of identifiers may be assessed by the device to determine that someone is consuming a product or type of product. For example, the combination of a chewing or swallowing sound and a package sound may indicate a product or type of product. The device may identify certain background noises and cancel the background noises, allowing for analysis on other sounds that may be more relevant to product consumption. The device or another device (e.g., the user device 106 and/or the one or more servers 140 of FIG. 1) may store and/or access data including related or different products. When a product has been identified (e.g., based on an audio profile match from received audio data of a person consuming the product or discussing the consumption of the product), the device may identify the product identifier of the product. For example, the matching sound profile for the product identified as being consumed may be stored on the device or the other device with data such as the product identifier, characteristics of the product, measurable attributes of the product, effects that the product has had on one or more users, and the like.

At block 454, the device may determine, based on the product identifier, one or more similar products (e.g., having one or more of the same characteristics or effects on a user as the identified product, products having one or more of the same ingredients, products having nutritional content within a range of the product, etc.) and/or one or more different products (e.g., products not having one or more of the same characteristics or user effects as the product, products known to cause the opposite effects of a user, products having nutritional content outside of a range of the product, etc.). For example, given a product identifier, the device or the other device may identify other products having similar characteristics (e.g., health characteristics, nutritional content, types of products, a same brand, same effects on a person's health, such as decreased heartrate or blood pressure, etc.) or substitute products (e.g., healthier products not known to cause the same level of effects such as heartrate or blood pressure changes, products with less content of certain ingredients such as sugar or fat, etc.).

At block 456, with user consent, the device may generate one or more messages for presentation (e.g., using the device or another device) based on one or more similar products or one or more different products. For example, as shown in FIG. 1, when the identified product is potato chips, the device may display a recommendation for a substitute product such as an apple. In such an example, the apple may be one of multiple products identified as having different characteristics, effects, ingredients, nutritional content, etc. from potato chips. The device may identify the potato chip product identifier (e.g., a specific potato chip product or a categorical product identifier for potato chips in general), and based on characteristics, measurable attributes, content, and/or effects stored in association with the product identifier, may find a corresponding product identifier stored with similar or different characteristics, measurable attributes, content, and/or effects. The messages may select one or more products or product categories (e.g., eat fruit instead of a less healthy product) and may include a recommendation, offer, incentive, or nutritional or health information for the similar or different product. For example, the messages may indicate similar products, similar products that are healthier, products that may be purchased nearby (e.g., within a distance threshold), substitute products, nutritional information for other products (e.g., content of nutritional ingredients such as sodium, fat, sugar, etc.), and/or health information (e.g., effects that a product may have on biomedical data such as heart rate, blood pressure, blood sugar, body temperature, etc.). The messages may be displayed using one or more methods, including text, graphs, audio, vibrations, and the like.

Referring to FIG. 4B, the process 450 may refer to one or more steps associated with block 414 of FIG. 4A.

Figure 4C:
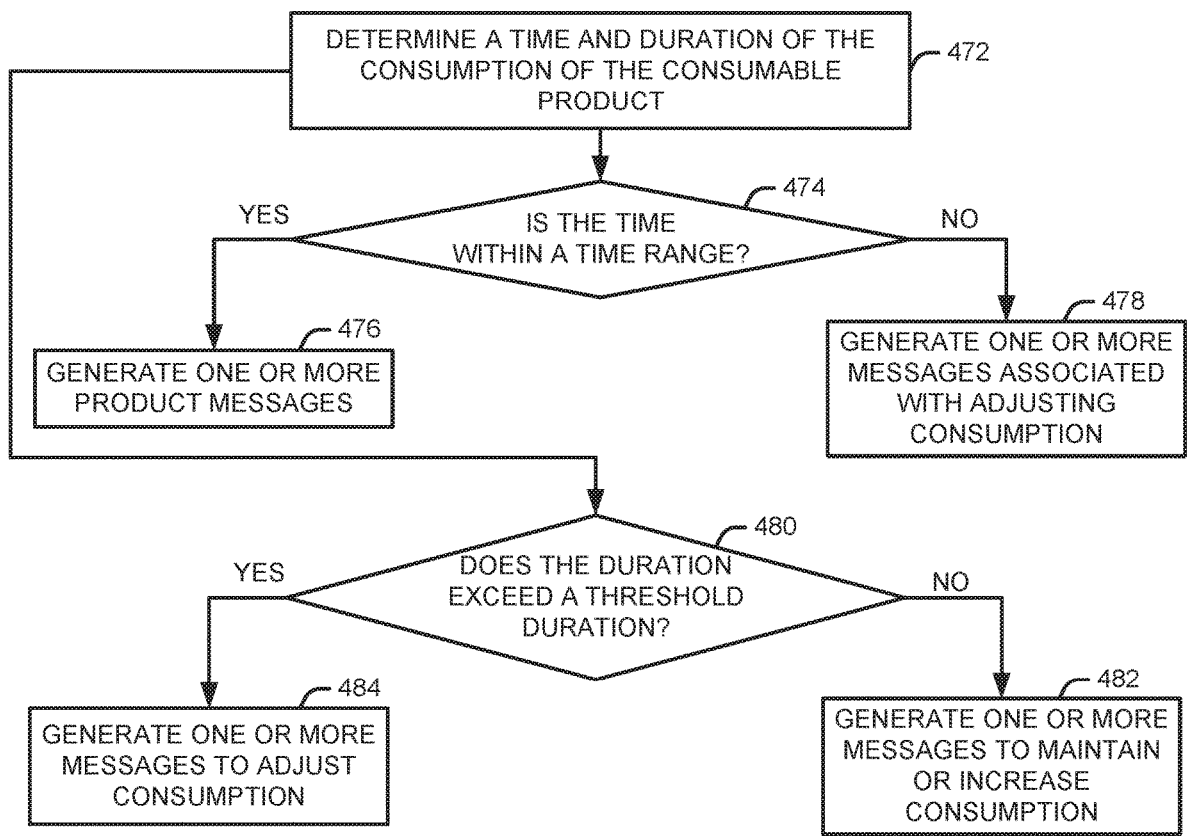
FIG. 4C illustrates a flow diagram for a process for detection and correction of eating behavior, in accordance with one or more example embodiments of the present disclosure.

FIG. 4C illustrates a flow diagram for a process 470 for detection and correction of eating behavior, in accordance with one or more example embodiments of the present disclosure.

At block 472, with user consent, a device (e.g., the wearable device 104 of FIG. 1) may determine a time and/or duration of a consumption of a consumable product (e.g., the product 206 of FIG. 2, the product 306 of FIG. 3). The time may refer to the time of day. For example, the device may determine the time when any portion of captured audio (e.g., the audio 208 of FIG. 2, the audio 308 of FIG. 3) occurred. The duration may refer to an entire time of a captured clip of audio, or to a portion of audio beginning when the device determines that the user is consuming a product and ending when the device determines that the user is no longer consuming a product (e.g., when the audio no longer matches a sound profile associated with consumption of a product).

At block 474, with user consent, the device may determine whether the time is within a time range. For example, certain time ranges may be associated with times when a person is expected to consume a product (e.g., meal times, times to take medicine or nutritional products, times to eat or drink based on a user's health, times to eat or drink based a user's schedule, times to eat or drink based on a user's exercise habits, times selected by a user, etc.). When the device determines that the consumption is within a time range (e.g., normal meal hours, times to take medicine, etc.), the device may continue to block 476. When the user is consuming a product outside of normal times (e.g., a late-night snack, taking medicine too soon, eating or drinking when the user's health or medical treatment does not allow eating or drinking), the device may proceed to block 478.

At block 476, with user consent, the device may generate one or more messages with information about one or more products. For example, if the product being consumed is associated with positive effects on the user, the messages may include offers or incentives to consume and/or purchase more of the product or similar products. The messages may encourage a user to continue to consume such products within the time range. The messages may include information or offers regarding substitute (e.g., healthier) products. The device may indicate that a user is chewing too loudly or talking while eating. At block 478, with user consent, the device may generate one or more messages discouraging consumption. For example, the messages may indicate that a user should not consume during this time, may suggest substitute products to consume, may sound alarms, and/or may notify other devices that the user is consuming a product outside of the approved time range.

At block 480, the device may determine whether the duration exceeds a threshold duration. For example, when a consumption time is limited to a duration (e.g., thirty minutes to complete a meal), and the duration exceeds the duration, the device may determine that the user is consuming too much. A drink of a liquid may be associated with the duration, which may correspond to an amount of liquid. For example, when a user is supposed to drink a certain amount of water, the duration may indicate whether the user consumed that amount, consumed too much, or consumed too little. The duration may be set based on user preferences and/or schedules, based on known meal times, or based on quantities of products to consume at a given time. When the duration is within the threshold duration, the device may proceed to block 482. When the duration exceeds the threshold duration, the device may continue to block 484.

At block 482, with user consent, the device may generate one or more messages encouraging a user to maintain the consumption level associated with the duration and/or to increase consumption. For example, when a user is expected to drink a certain volume of water associated with the duration, and the user's consumption time for the liquid is below the threshold duration, the device may generate messages encouraging the user to drink more water. When the user is determined to be eating for a time within the threshold duration, the device may determine that the user has not eaten too much or too long, and may generate messages encouraging the use to continue to eat within the threshold duration of time.

At block 484, with user consent, the device may generate one or more messages encouraging a user to reduce consumption. For example, if the user is determined to be eating a product for a duration longer than the threshold duration, the device may generate messages reminding a user of the duration, indicating the nutritional content of the product, or indicating the effects that the product may have on one or more measurable attributes.

Referring to FIG. 4C, the process 470 may refer to one or more steps associated with block 414 of FIG. 4A.

Figure 4D:
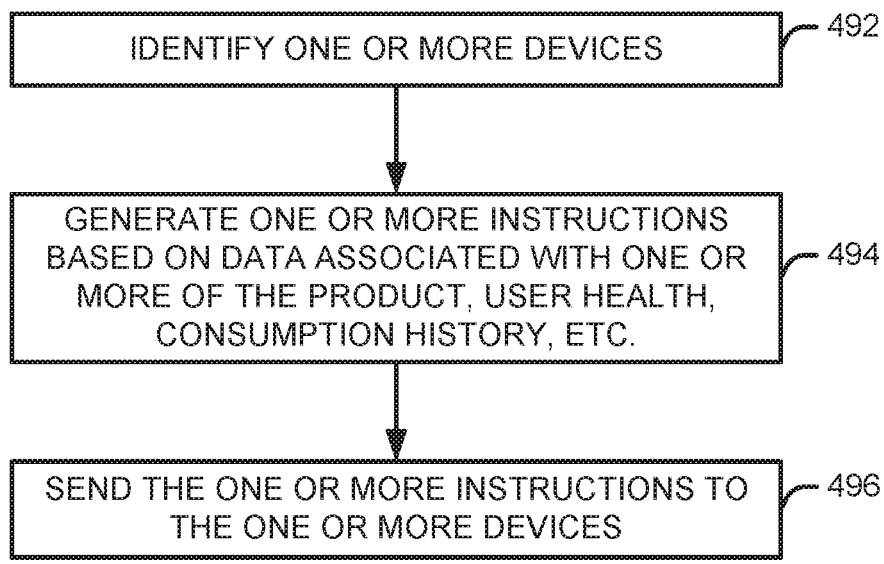
FIG. 4D illustrates a flow diagram for a process for detection and correction of eating behavior, in accordance with one or more example embodiments of the present disclosure.

FIG. 4D illustrates a flow diagram for a process 490 for detection and correction of eating behavior, in accordance with one or more example embodiments of the present disclosure.

At block 492, with user consent, a device (e.g., the wearable device 104 of FIG. 1) may identify one or more devices (e.g., the user device 106, the one or more devices 150 of FIG. 1). For example, block 492 represent actions corresponding to block 414 of FIG. 4A. When the device has identified that a user is consuming a product, has obtained data for a measurable attribute of the product, and has analyzed the data, the device may identify one or more devices to which to send instructions or messages.

At block 494, the device may generate one or more instructions based on the data for the product. For example, when the device determines that a user is consuming a product, the device may generate a notification for a smart refrigerator or other smart device (e.g., a smart microwave) to log the consumption, to display or otherwise output messages requesting that the person adjust consumption behavior (e.g., to prevent dispensing a product, to block access to a product, to change or stop operation, etc.). The instructions may indicate to a device to stop recording or otherwise detecting data (e.g., stop recording audio, stop or change collection of biomedical data, etc.). At block 496, the device may send the one or more instructions. The instructions may be sent directly to a device, or may be sent through another device (e.g., the user device 106, the one or more servers 140 of FIG. 1).

Figure 5:
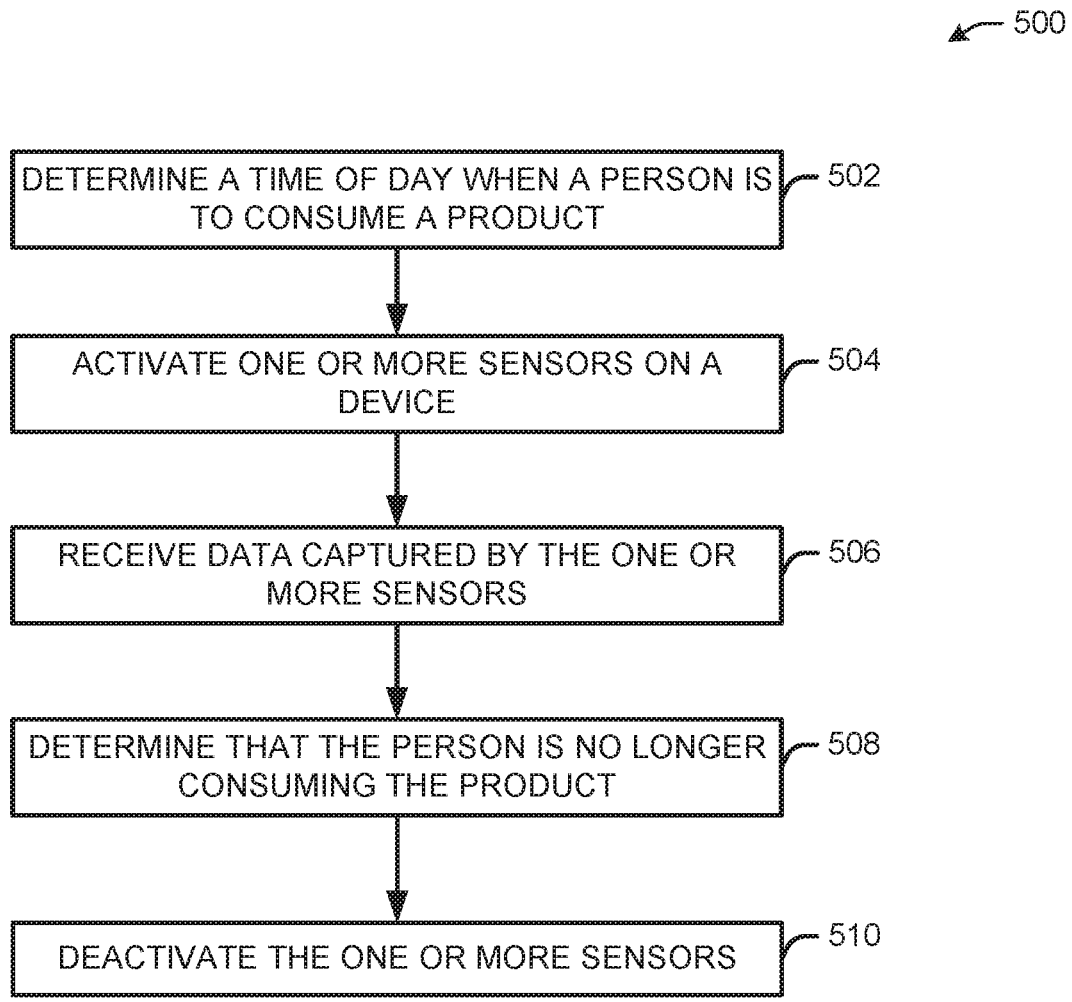
FIG. 5 illustrates a flow diagram for a process for detection and correction of eating behavior, in accordance with one or more example embodiments of the present disclosure.

FIG. 5 illustrates a flow diagram for a process 500 for detection and correction of eating behavior, in accordance with one or more example embodiments of the present disclosure.

At block 502, with user consent, a device (e.g., the wearable device 104 of FIG. 1) may determine a time of day when a user is to consume a product (e.g., the product 206 of FIG. 2, the product 306 of FIG. 3). The time of day may correspond to meal times, times when a user is to take a medicinal or other health product, times set based on a user's schedule, times when a user is known to perform activities (e.g., exercising), or other times. The times may be preset, selected by users, or based on data (e.g., calendar data from an application executing on the device or another device).

At block 504, with user consent, the device may activate one or more sensors on the device. Activating may include powering on a sensor or changing the operating state of a sensors, such as modifying a sampling rate or frequency. For example, when the sensors are microphones, the device may activate a microphone by powering on the microphone and/or by setting a sampling rate or frequency with which to capture audio. The sensors may capture audio at one sampling rate or frequency, and based on the time of day, the device may change (e.g., increase) the sampling rate or frequency for more data to analyze over a time period.

At block 506, with user consent, the device may receive captured data by the one or more sensors. Captured audio data may be analyzed by the device or sent to another device for analysis. The audio data may be converted to a sound profile. For example, a sound profile may include a frequency distribution of captured audio signals over time. A device may compare the sound profile to known sound profiles of consumable products. For example, the crunch of potato chips may match a known sound profile for potato chips. The crisp sound of a user biting into an apple may have a distinct sound profile, as may the sound of swallowing a liquid, opening a carbonated beverage or bag, opening and closing a refrigerator, an active microwave, and the like. Audio profiles of consumable products may be differentiated from audio profiles of other types of noises or sounds, such as talking (e.g., voice) or certain types of background noise (e.g., sounds of musical instruments, automobiles, computer devices, etc.). Machine learning using neural networks or other types of machines may be used to identify sounds and words to identify when a user is consuming a product, about to consume a product, and has recently consumed a product. Using sound profiles, a device may determine a specific product or type of product that a person may be consuming.

At block 508, the device may determine that the user is no longer consuming the product. The device may determine, based on captured audio, that the use is no longer consuming a product based on whether the captured audio matches audio associated with a known product and when the audio no longer matches audio associated with a known product.

At block 510, the device may deactivate the one or more sensors. For example, the device may deactivate (e.g., lower power, sampling rate, or frequency) the one or more sensors when the time of day (or time period of day) has passed.

Figure 6:
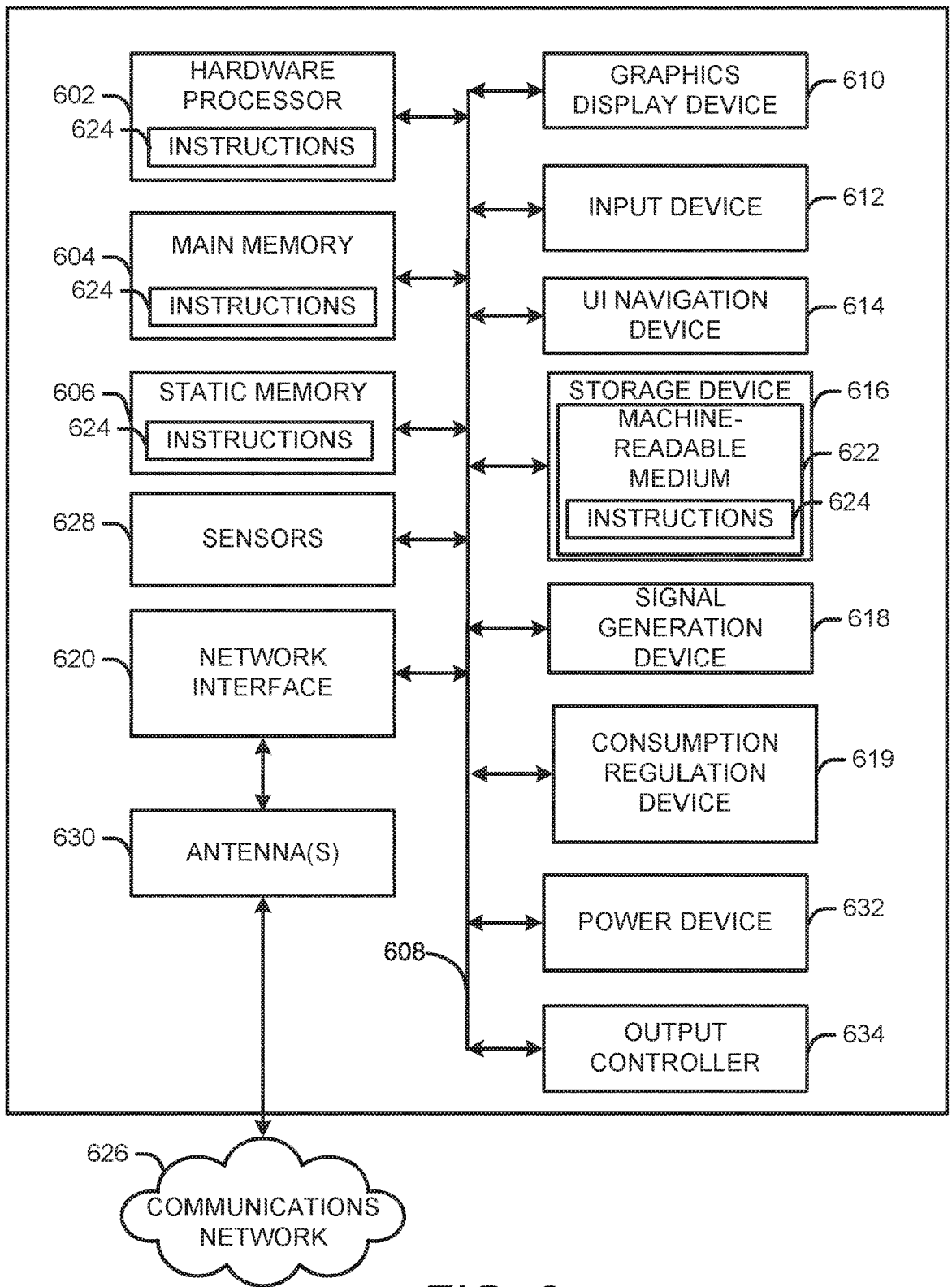
FIG. 6 illustrates a block diagram of an example machine upon which any of one or more techniques (e.g., methods) may be performed, in accordance with one or more example embodiments of the present disclosure.

FIG. 6 illustrates a block diagram of an example of a machine 600 (e.g., implemented in whole or in part by the wearable device 104 of FIG. 1, the user device 106 of FIG. 1, the one or more servers 140 of FIG. 1, the device 108 of FIG. 1, the device 110 of FIG. 1, the one or more devices 150 of FIG. 1, the wearable device 204 of FIG. 2, the wearable device 304 of FIG. 3) or system upon which any one or more of the techniques (e.g., methodologies) discussed herein may be performed. In other embodiments, the machine 600 may operate as a standalone device or may be connected (e.g., networked) to other machines. In a networked deployment, the machine 600 may operate in the capacity of a server machine, a client machine, or both in server-client network environments. In an example, the machine 600 may act as a peer machine in Wi-Fi direct, peer-to-peer (P2P) (or other distributed) network environments. The machine 600 may be a wearable device or any machine capable of executing instructions (sequential or otherwise) that specify actions to be taken by that machine. Further, while only a single machine is illustrated, the term "machine" shall also be taken to include any collection of machines that individually or jointly execute a set (or multiple sets) of instructions to perform any one or more of the methodologies discussed herein, such as cloud computing, software as a service (SaaS), or other computer cluster configurations.

Examples, as described herein, may include or may operate on logic or a number of components, modules, or mechanisms. Modules are tangible entities (e.g., hardware) capable of performing specified operations when operating. A module includes hardware. In an example, the hardware may be specifically configured to carry out a specific operation (e.g., hardwired). In another example, the hardware may include configurable execution units (e.g., transistors, circuits, etc.) and a computer readable medium containing instructions where the instructions configure the execution units to carry out a specific operation when in operation. The configuring may occur under the direction of the executions units or a loading mechanism. Accordingly, the execution units are communicatively coupled to the computer-readable medium when the device is operating. In this example, the execution units may be a member of more than one module. For example, under operation, the execution units may be configured by a first set of instructions to implement a first module at one point in time and reconfigured by a second set of instructions to implement a second module at a second point in time.

The machine (e.g., computer system) 600 may include any combination of the illustrated components. For example, the machine 600 may include a hardware processor 602 (e.g., a central processing unit (CPU), a graphics processing unit (GPU), a hardware processor core, or any combination thereof), a main memory 604 and a static memory 606, some or all of which may communicate with each other via an interlink (e.g., bus) 608. The machine 600 may further include a power management device 632, a graphics display device 610, an alphanumeric input device 612 (e.g., a keyboard), and a user interface (UI) navigation device 614 (e.g., a mouse). In an example, the graphics display device 610, alphanumeric input device 612, and UI navigation device 614 may be a touch screen display. The machine 600 may additionally include a storage device (i.e., drive unit) 616, a signal generation device 618 (e.g., a biomedical data signal or other data signal), a consumption regulation device 619, a network interface device/transceiver 620 coupled to antenna(s) 630, and one or more sensors 628, such as a sound detecting sensor (e.g., a microphone), one or more electromyography sensors (e.g., to detect swallowing), accelerometers, magnetometers, location sensors, and the like. When using multiple sensors 628, the sensors may be arranged to detect sounds in different directions and at different distances. The machine 600 may include an output controller 634, such as a serial (e.g., universal serial bus (USB), parallel, or other wired or wireless (e.g., infrared (IR), near field communication (NFC), etc.) connection to communicate with or control one or more peripheral devices (e.g., a printer, a card reader, other sensors, etc.)).

The storage device 616 may include a machine readable medium 622 on which is stored one or more sets of data structures or instructions 624 (e.g., software) embodying or utilized by any one or more of the techniques or functions described herein. The instructions 624 may also reside, completely or at least partially, within the main memory 604, within the static memory 606, or within the hardware processor 602 during execution thereof by the machine 600. In an example, one or any combination of the hardware processor 602, the main memory 604, the static memory 606, or the storage device 616 may constitute machine-readable media.

The consumption regulation device 619 may carry out or perform any of the operations and processes (e.g., process 400 of FIG. 4A, process 450 of FIG. 4B, process 470 of FIG. 4C, process 490 of FIG. 4D, process 500 of FIG. 5) described and shown above.

In one or more embodiments, the consumption regulation device 619 may be implemented a wearable device (e.g., the wearable device 104 of FIG. 1) or as a medical device (e.g., the device 108 or the device 110 of FIG. 1). The consumption regulation device 619 may record audio (with a user's consent) using one or more audio sensors (e.g., the one or more sensors 628). Captured audio data may be analyzed by the consumption regulation device 619 or sent to another device (e.g., the user device 106 or the one or more servers 140 of FIG. 1) for analysis.

In one or more embodiments, the consumption regulation device 619 may be implemented in a user device (e.g., the user device 106) or a server device (e.g., the one or more servers 150 of FIG. 1). The consumption regulation device 619 may convert audio data to a sound profile. For example, a sound profile may include a frequency distribution of captured audio signals over time. The consumption regulation device 619 may compare the sound profile to known sound profiles of consumable products. The consumption regulation device 619 may differentiate audio profiles of consumable products from audio profiles of other types of noises or sounds, such as talking (e.g., voice) or certain types of background noise (e.g., sounds of musical instruments, automobiles, computer devices, etc.). The consumption regulation device 619 may be used to identify sounds and words to identify when a user is consuming a product, about to consume a product, and has recently consumed a product. Using sound profiles, the consumption regulation device 619 may determine a specific product or type of product that a person may be consuming.

In one or more embodiments, the consumption regulation device 619 may determine characteristics of a product once the product has been identified. For example, a cheeseburger may have high cholesterol and may trigger a higher blood pressure for a person, as may potato chips or other foods known to be salty. Candy may include sugar which may cause an increase in a person's blood glucose levels. Spicy or acidic products may cause indigestion or acid reflux. A caffeinated product may increase a person's heart rate. When the consumption regulation device 619 determines the product or type of product that a person may be consuming, the device may determine corresponding characteristics of the product, and may determine data which may be associated with the effects of the characteristics. For example, if a characteristic of a sugary food or drink is to increase blood glucose levels, the consumption regulation device 619 may determine that blood glucose data may indicate the effects of consuming the sugary food or drink. When caffeine products are known to increase heartrate, the consumption regulation device 619 may determine that monitoring a user's heartrate may provide an indication of the effects of consuming caffeine.

In one or more embodiments, the consumption regulation device 619 (e.g., when implemented on the wearable device 104 of FIG. 1) may determine that another device or an application is responsible for detecting or otherwise collecting data associated with a characteristic of a consumable product. For example, a blood glucose monitor may measure blood glucose levels. A heartrate monitor may capture heartrate data. A hydration sensor may measure a user's dehydration. An accelerometer, magnetometer, wireless signals (e.g., Bluetooth or Wi-Fi signals), global navigation satellite system signals may be used (with a user's consent) to determine a device's motion or location, and the motion or location data may confirm if the user is at a location (e.g., a restaurant) or moving (e.g., motioning an arm or hand toward the face) in a manner which indicates a likely consumption of a product (e.g., and may be used to supplement audio data for the purpose of determining when a user is consuming a product). A hydrogen sensor may measure a user's indigestion. When the consumption regulation device 619 determines a characteristic of a consumable product and an associated type of data which may measure the effects of the characteristic on a person consuming the consumable product, the consumption regulation device 619 may identify another device or an application responsible for capturing the associated type of data, and may request the associated data. The request for the data may include specification of a sampling rate or frequency. For example, consumption regulation device 619 may request that another device provide data captured at a particular rate or frequency (e.g., a higher sampling rate or frequency than normal). Such may allow devices to conserve power and resources (e.g., by not sampling at higher rates or frequencies unless a user is consuming something).

In one or more embodiments, with a user's consent, the consumption regulation device 619 may help a user regulate their intake of consumable products and may provide recommendations for products, when to consume or not consume, locations where consumable products are available, nutritional information, warnings/alerts, alarms to medical professionals or other parties or devices, and the like. For example, when the consumption regulation device 619 detects that a user is eating food late at night (e.g., outside of a normal window of time associated with eating meals), the consumption regulation device 619 may present alarms or messages encouraging the user to eat something healthier or to wait until the next meal, or to indicate the effects that consuming a product may have on the person. The de consumption regulation device 619 vice may provide recommendations of healthier products to substitute, such as substituting fruit and vegetables for a less healthy product.

In one or more embodiments, the consumption regulation device 619 may be implemented at the one or more servers 140 of FIG. 1 to receive data from the wearable device 104 or the user device 106 of FIG. 1. For example, the consumption regulation device 619 may receive captured audio data and determine that the user is consuming one or more products. The consumption regulation device 619, implemented at the one or more servers 140, the wearable device 104, and/or the user device 106 of FIG. 1 may determine characteristics and measurable attributes of a product. The consumption regulation device 619 may request additional data for the measurable attributes, including by specifying a frequency, sampling rate, time, and/or format of the data.

In one or more embodiments, the consumption regulation device 619 may be implemented at the one or more devices 150 of FIG. 1. For example, the consumption regulation device 619 may record data of a user such as biomedical data, exercise data, consumption data, product inventory (e.g., a smart refrigerator or freezer), and may send and receive data associated with consumption recommendations, exercise recommendations, etc.

It is understood that the above are only a subset of what the consumption regulation device 619 may be configured to perform and that other functions included throughout this disclosure may also be performed by the consumption regulation device 619.

While the machine-readable medium 622 is illustrated as a single medium, the term "machine-readable medium" may include a single medium or multiple media (e.g., a centralized or distributed database, and/or associated caches and servers) configured to store the one or more instructions 624.

Various embodiments may be implemented fully or partially in software and/or firmware. This software and/or firmware may take the form of instructions contained in or on a non-transitory computer-readable storage medium. Those instructions may then be read and executed by one or more processors to enable performance of the operations described herein. The instructions may be in any suitable form, such as but not limited to source code, compiled code, interpreted code, executable code, static code, dynamic code, and the like. Such a computer-readable medium may include any tangible non-transitory medium for storing information in a form readable by one or more computers, such as but not limited to read only memory (ROM); random access memory (RAM); magnetic disk storage media; optical storage media; a flash memory, etc.

The term "machine-readable medium" may include any medium that is capable of storing, encoding, or carrying instructions for execution by the machine 600 and that cause the machine 600 to perform any one or more of the techniques of the present disclosure, or that is capable of storing, encoding, or carrying data structures used by or associated with such instructions. Non-limiting machine-readable medium examples may include solid-state memories and optical and magnetic media. In an example, a massed machine-readable medium includes a machine-readable medium with a plurality of particles having resting mass. Specific examples of massed machine-readable media may include non-volatile memory, such as semiconductor memory devices (e.g., electrically programmable read-only memory (EPROM), or electrically erasable programmable read-only memory (EEPROM)) and flash memory devices; magnetic disks, such as internal hard disks and removable disks; magneto-optical disks; and CD-ROM and DVD-ROM disks.

The instructions 624 may further be transmitted or received over a communications network 626 using a transmission medium via the network interface device/transceiver 620 utilizing any one of a number of transfer protocols (e.g., frame relay, internet protocol (IP), transmission control protocol (TCP), user datagram protocol (UDP), hypertext transfer protocol (HTTP), etc.). Example communications networks may include a local area network (LAN), a wide area network (WAN), a packet data network (e.g., the Internet), mobile telephone networks (e.g., cellular networks), plain old telephone (POTS) networks, wireless data networks (e.g., Institute of Electrical and Electronics Engineers (IEEE) 802.11 family of standards known as Wi-Fi®, IEEE 802.16 family of standards known as WiMax®), IEEE 802.15.4 family of standards, and peer-to-peer (P2P) networks, among others. In an example, the network interface device/transceiver 620 may include one or more physical jacks (e.g., Ethernet, coaxial, or phone jacks) or one or more antennas to connect to the communications network 626. In an example, the network interface device/transceiver 620 may include a plurality of antennas to wirelessly communicate using at least one of single-input multiple-output (SIMO), multiple-input multiple-output (MIMO), or multiple-input single-output (MISO) techniques. The term "transmission medium" shall be taken to include any intangible medium that is capable of storing, encoding, or carrying instructions for execution by the machine 600 and includes digital or analog communications signals or other intangible media to facilitate communication of such software.

The operations and processes described and shown above may be carried out or performed in any suitable order as desired in various implementations. Additionally, in certain implementations, at least a portion of the operations may be carried out in parallel. Furthermore, in certain implementations, less than or more than the operations described may be performed.

The word "exemplary" is used herein to mean "serving as an example, instance, or illustration." Any embodiment described herein as "exemplary" is not necessarily to be construed as preferred or advantageous over other embodiments. The terms "computing device," "user device," "communication station," "station," "handheld device," "mobile device," "wireless device" and "user equipment" (UE) as used herein refers to a wireless communication device such as a cellular telephone, a smartphone, a tablet, a netbook, a wireless terminal, a laptop computer, a femtocell, a high data rate (HDR) subscriber station, an access point, a printer, a point of sale device, an access terminal, or other personal communication system (PCS) device. The device may be either mobile or stationary.

As used within this document, the term "communicate" is intended to include transmitting, or receiving, or both transmitting and receiving. This may be particularly useful in claims when describing the organization of data that is being transmitted by one device and received by another, but only the functionality of one of those devices is required to infringe the claim. Similarly, the bidirectional exchange of data between two devices (both devices transmit and receive during the exchange) may be described as "communicating," when only the functionality of one of those devices is being claimed. The term "communicating" as used herein with respect to a wireless communication signal includes transmitting the wireless communication signal and/or receiving the wireless communication signal. For example, a wireless communication unit, which is capable of communicating a wireless communication signal, may include a wireless transmitter to transmit the wireless communication signal to at least one other wireless communication unit, and/or a wireless communication receiver to receive the wireless communication signal from at least one other wireless communication unit.

As used herein, unless otherwise specified, the use of the ordinal adjectives "first," "second," "third," etc., to describe a common object, merely indicates that different instances of like objects are being referred to and are not intended to imply that the objects so described must be in a given sequence, either temporally, spatially, in ranking, or in any other manner.

Some embodiments may be used in conjunction with various devices and systems, for example, a personal computer (PC), a desktop computer, a mobile computer, a laptop computer, a notebook computer, a tablet computer, a server computer, a handheld computer, a handheld device, a personal digital assistant (PDA) device, a handheld PDA device, an on-board device, an off-board device, a hybrid device, a vehicular device, a non-vehicular device, a mobile or portable device, a consumer device, a non-mobile or non-portable device, a wireless communication station, a wireless communication device, a wireless access point (AP), a wired or wireless router, a wired or wireless modem, a video device, an audio device, an audio-video (A/V) device, a wired or wireless network, a wireless area network, a wireless video area network (WVAN), a local area network (LAN), a wireless LAN (WLAN), a personal area network (PAN), a wireless PAN (WPAN), and the like.

Some embodiments may be used in conjunction with one way and/or two-way radio communication systems, biomedical sensors, wearable devices or sensors, cellular radio-telephone communication systems, a mobile phone, a cellular telephone, a wireless telephone, a personal communication system (PCS) device, a PDA device which incorporates a wireless communication device, a mobile or portable global positioning system (GPS) device, a device which incorporates a GPS receiver or transceiver or chip, a device which incorporates an RFID element or chip, a multiple input multiple output (MIMO) transceiver or device, a single input multiple output (SIMO) transceiver or device, a multiple input single output (MISO) transceiver or device, a device having one or more internal antennas and/or external antennas, digital video broadcast (DVB) devices or systems, multi-standard radio devices or systems, a wired or wireless handheld device, e.g., a smartphone, a wireless application protocol (WAP) device, or the like.

Some embodiments may be used in conjunction with one or more types of wireless communication signals and/or systems following one or more wireless communication protocols, for example, radio frequency (RF), infrared (IR), frequency-division multiplexing (FDM), orthogonal FDM (OFDM), time-division multiplexing (TDM), time-division multiple access (TDMA), extended TDMA (E-TDMA), general packet radio service (GPRS), extended GPRS, code-division multiple access (CDMA), wideband CDMA (WCDMA), CDMA 2000, single-carrier CDMA, multi-carrier CDMA, multi-carrier modulation (MDM), discrete multi-tone (DMT), Bluetooth®, global positioning system (GPS), Wi-Fi, Wi-Max, ZigBee, ultra-wideband (UWB), global system for mobile communications (GSM), 2G, 2.5G, 3G, 3.5G, 4G, fifth generation (5G) mobile networks, 3GPP, long term evolution (LTE), LTE advanced, enhanced data rates for GSM Evolution (EDGE), or the like. Other embodiments may be used in various other devices, systems, and/or networks.

It is understood that the above descriptions are for purposes of illustration and are not meant to be limiting.

Although specific embodiments of the disclosure have been described, one of ordinary skill in the art will recognize that numerous other modifications and alternative embodiments are within the scope of the disclosure. For example, any of the functionality and/or processing capabilities described with respect to a particular device or component may be performed by any other device or component. Further, while various illustrative implementations and architectures have been described in accordance with embodiments of the disclosure, one of ordinary skill in the art will appreciate that numerous other modifications to the illustrative implementations and architectures described herein are also within the scope of this disclosure.

Program module(s), applications, or the like disclosed herein may include one or more software components including, for example, software objects, methods, data structures, or the like. Each such software component may include computer-executable instructions that, responsive to execution, cause at least a portion of the functionality described herein (e.g., one or more operations of the illustrative methods described herein) to be performed.

A software component may be coded in any of a variety of programming languages. An illustrative programming language may be a lower-level programming language such as an assembly language associated with a particular hardware architecture and/or operating system platform. A software component comprising assembly language instructions may require conversion into executable machine code by an assembler prior to execution by the hardware architecture and/or platform.

Another example programming language may be a higher-level programming language that may be portable across multiple architectures. A software component comprising higher-level programming language instructions may require conversion to an intermediate representation by an interpreter or a compiler prior to execution.

Other examples of programming languages include, but are not limited to, a macro language, a shell or command language, a job control language, a script language, a database query or search language, or a report writing language. In one or more example embodiments, a software component comprising instructions in one of the foregoing examples of programming languages may be executed directly by an operating system or other software component without having to be first transformed into another form.

A software component may be stored as a file or other data storage construct. Software components of a similar type or functionally related may be stored together such as, for example, in a particular directory, folder, or library. Software components may be static (e.g., pre-established or fixed) or dynamic (e.g., created or modified at the time of execution).

Software components may invoke or be invoked by other software components through any of a wide variety of mechanisms. Invoked or invoking software components may comprise other custom-developed application software, operating system functionality (e.g., device drivers, data storage (e.g., file management) routines, other common routines and services, etc.), or third-party software components (e.g., middleware, encryption, or other security software, database management software, file transfer or other network communication software, mathematical or statistical software, image processing software, and format translation software).

Software components associated with a particular solution or system may reside and be executed on a single platform or may be distributed across multiple platforms. The multiple platforms may be associated with more than one hardware vendor, underlying chip technology, or operating system. Furthermore, software components associated with a particular solution or system may be initially written in one or more programming languages, but may invoke software components written in another programming language.

Computer-executable program instructions may be loaded onto a special-purpose computer or other particular machine, a processor, or other programmable data processing apparatus to produce a particular machine, such that execution of the instructions on the computer, processor, or other programmable data processing apparatus causes one or more functions or operations specified in any applicable flow diagrams to be performed. These computer program instructions may also be stored in a computer-readable storage medium (CRSM) that upon execution may direct a computer or other programmable data processing apparatus to function in a particular manner, such that the instructions stored in the computer-readable storage medium produce an article of manufacture including instruction means that implement one or more functions or operations specified in any flow diagrams. The computer program instructions may also be loaded onto a computer or other programmable data processing apparatus to cause a series of operational elements or steps to be performed on the computer or other programmable apparatus to produce a computer-implemented process.

Additional types of CRSM that may be present in any of the devices described herein may include, but are not limited to, programmable random access memory (PRAM), SRAM, DRAM, RAM, ROM, electrically erasable programmable read-only memory (EEPROM), flash memory or other memory technology, compact disc read-only memory (CD-ROM), digital versatile disc (DVD) or other optical storage, magnetic cassettes, magnetic tape, magnetic disk storage or other magnetic storage devices, or any other medium which can be used to store the information and which can be accessed. Combinations of any of the above are also included within the scope of CRSM. Alternatively, computer-readable communication media (CRCM) may include computer-readable instructions, program module(s), or other data transmitted within a data signal, such as a carrier wave, or other transmission. However, as used herein, CRSM does not include CRCM.

Although embodiments have been described in language specific to structural features and/or methodological acts, it is to be understood that the disclosure is not necessarily limited to the specific features or acts described. Rather, the specific features and acts are disclosed as illustrative forms of implementing the embodiments. Conditional language, such as, among others, "can," "could," "might," or "may," unless specifically stated otherwise, or otherwise understood within the context as used, is generally intended to convey that certain embodiments could include, while other embodiments do not include, certain features, elements, and/or steps. Thus, such conditional language is not generally intended to imply that features, elements, and/or steps are in any way required for one or more embodiments or that one or more embodiments necessarily include logic for deciding, with or without user input or prompting, whether these features, elements, and/or steps are included or are to be performed in any particular embodiment.

What is claimed is:

1. A method, comprising:
    receiving, at a wrist-worn device, first data detected by the wrist-worn device, wherein the first data comprise audio data indicative of consumption of a product by a user wearing the wrist-worn device;
    identifying, based on the audio data, a sound profile indicating that a first type of food or liquid was consumed;
    determining, based on the sound profile, one or more scores indicative of types of food or liquid, wherein a first score of the one or more scores indicates that the first type of food or liquid was consumed by the user;
    determining that the first score exceeds a score threshold;
    determining, based on the first score exceeding the score threshold, that the product is the first type of food or liquid;
    determining, based on the first type of food or liquid, a characteristic associated with the product;
    determining a first device associated with detecting a measurable attribute associated with the characteristic;
    sending a request to the first device to increase a sampling rate or frequency at which to detect second data associated with the measurable attribute, the request comprising an indication of the sampling rate or frequency and a time period during which to apply the sampling rate or frequency;
    receiving, by the wrist-worn device, the second data detected using the sampling rate or frequency;
    generating, based on the second data, one or more messages associated with consumption of the first type of food or liquid; and
    displaying the one or more messages.

2. The method of claim 1, wherein determining the first device comprises determining an application associated with detecting the second data using the first device, and wherein the request further comprises an indication that the application provides the second data based on the sampling rate or frequency.

3. The method of claim 1, wherein the second data comprises at least one of blood glucose, heartrate, perspiration, electrocardiogram data, or hydrogen data.

4. The method of claim 1, further comprising determining at least one of a duration or a time associated with the consumption of the food or liquid, wherein generating the one or more messages is further based on the at least one of the duration or the time.

5. A method, comprising:
receiving, at a first device, audio data of a user;
identifying, based on the audio data, a sound profile indicating that a first product was consumed;
determining, based on a comparison of a score of the sound profile to a threshold, that the first product was consumed by the user, wherein the score is indicative of a likelihood that the user consumed the first product;
determining, based on the product, a measurable attribute associated with the user;
determining, based on the measurable attribute, first data;
sending a request to increase a sampling rate or frequency at which to detect the first data, the request comprising an indication of the sampling rate or frequency and a time period during which to apply the sampling rate or frequency; and
receiving the first data.

6. The method of claim 5, further comprising:
determining an application associated with the measurable attribute, wherein
the request further comprises an indication of the application.

7. The method of claim 5, wherein the first device comprises one or more sensors, further comprising:
determining a time of day associated with receiving the audio data; and
activating the one or more sensors based on the time of day, wherein at least a portion of the audio data is captured by the one or more sensors, and wherein activating comprises adjusting a sampling rate or frequency of the one or more sensors from a non-zero sampling rate or frequency to an increased sampling rate or frequency.

8. The method of claim 5, wherein the audio data comprises first audio data received by a first sensor and second audio data received by a second sensor, wherein the first audio data is indicative of chewing or swallowing, and wherein the second audio data comprises audio associated with a package or container.

9. The method of claim 5, further comprising:
determining a time associated with the consumption of the product; and
generating a message based on the time.

10. The method of claim 5, wherein the first device comprises one or more sensors, further comprising:
determining a location of the first device; and
activating the one or more sensors based on the location, wherein at least a portion of the audio data is captured by the one or more sensors.

11. The method of claim 5, comprising:
determining, based on the audio data, one or more scores indicative of types of food or liquid, wherein the one or more scores comprises the score, and wherein determining the one or more scores comprises matching the audio data to the sound profile;
determining that the score exceeds the threshold; and
determining, based on the score exceeding the threshold, that the product is a first type of food or liquid, wherein determining the measurable attribute is based on the first type of food or liquid.

12. The method of claim 5, further comprising:
determining a duration associated with the consumption of the product; and
generating a message based on the duration.

13. The method of claim 5, wherein the product is a first product, further comprising:
determining a second product associated with the measurable attribute; and
generating a message comprising an indication of the second product.

14. The method of claim 5, wherein the product is a first product, further comprising:
determining a second product unassociated with the measurable attribute; and
generating a message comprising an indication of the second product.

15. The method of claim 5, further comprising:
determining a movement of the first device; and
determining that the movement is indicative of the consumption of the product.

16. The method of claim 5, further comprising:
determining an orientation of the first device; and
determining that the orientation is indicative of the consumption of the product.

17. A device comprising memory coupled to at least one processor, wherein the at least one processor is configured to:
receive audio data of a user;
identify, based on the audio data, a sound profile indicating that a product was consumed;
determine, based on a comparison of a score of the sound profile to a threshold, that the product was consumed by the user, wherein the score is indicative of a likelihood that the user consumed the product;
determine, based on the product, a measurable attribute associated with the user;
determine, based on the measurable attribute, first data;
sending a request to increase a sampling rate or frequency at which to detect the first data, the request comprising an indication of the sampling rate or frequency and a time period during which to apply the sampling rate or frequency; and
receive the first data.

18. The device of claim 17, wherein to identify the sound profile is based on a frequency distribution of the audio data.

* * * * *